(12) United States Patent
Langella et al.

US010238697B2

(10) Patent No.: US 10,238,697 B2
(45) Date of Patent: Mar. 26, 2019

(54) LACTOCOCCUS LACTIS PRODUCING TSLP OR IL-25 AND THEIR USES AS PROBIOTICS AND THERAPEUTICS

(71) Applicant: ARES TRADING S.A., Aubonne (CH)

(72) Inventors: Philippe Langella, Velizy (FR); Jean-Marc Chatel, Meudon (FR); Luis Bermudez-Humaran, Jouy-en-Josas (FR); Camille Aubry, Saint-Germain-en-Laye (FR); Laurence Goffin, Ornex (FR); Simone Favre-Zimmerli, Burlington, MA (US); Yolande Chvatchko, Confignon (CH)

(73) Assignee: ARES TRADING S.A., Aubonne (CH)

( * ) Notice: Subject to any disclaimer, the term of this patent is extended or adjusted under 35 U.S.C. 154(b) by 0 days.

(21) Appl. No.: 15/565,958

(22) PCT Filed: Apr. 12, 2016

(86) PCT No.: PCT/EP2016/058020
§ 371 (c)(1),
(2) Date: Oct. 12, 2017

(87) PCT Pub. No.: WO2016/166104
PCT Pub. Date: Oct. 20, 2016

(65) Prior Publication Data
US 2018/0104285 A1  Apr. 19, 2018

(30) Foreign Application Priority Data
Apr. 15, 2015 (EP) ..................... 15163637

(51) Int. Cl.
| A61P 1/00 | (2006.01) |
|---|---|
| A61P 1/04 | (2006.01) |
| C07K 14/52 | (2006.01) |
| A61K 35/744 | (2015.01) |
| A61K 38/20 | (2006.01) |
| C12N 15/74 | (2006.01) |
| A61K 38/19 | (2006.01) |
| C07K 14/315 | (2006.01) |
| C07K 14/54 | (2006.01) |
| A23L 33/00 | (2016.01) |
| A23L 33/135 | (2016.01) |
| A61P 37/02 | (2006.01) |
| A61P 29/00 | (2006.01) |
| A61K 45/06 | (2006.01) |
| A61K 35/00 | (2006.01) |

(52) U.S. Cl.
CPC .......... *A61K 35/744* (2013.01); *A23L 33/135* (2016.08); *A23L 33/30* (2016.08); *A61K 38/19* (2013.01); *A61K 38/20* (2013.01); *A61K 45/06* (2013.01); *A61P 1/00* (2018.01); *A61P 1/04* (2018.01); *A61P 29/00* (2018.01); *A61P 37/02* (2018.01); *C07K 14/315* (2013.01); *C07K 14/52* (2013.01); *C07K 14/54* (2013.01); *C12N 15/746* (2013.01); *A23V 2002/00* (2013.01); *A23Y 2240/41* (2013.01); *A61K 2035/115* (2013.01)

(58) Field of Classification Search
None
See application file for complete search history.

(56) References Cited

U.S. PATENT DOCUMENTS

2009/0148389 A1* 6/2009 Rottiers ............... A61K 35/747
424/45
2015/0139940 A1 5/2015 Bermudez Humaran et al.

OTHER PUBLICATIONS

Foligne, B. et al. "Prevention and Treatment of Colitis With *Lactococcus lactis* Secreting the Immunomodulatory *Yersinia* LcrV Protein" *Gastroenterology*, Sep. 1, 2007, pp. 862-874, vol. 133, No. 3.
Liu, Y-J. "Thymic stromal lymphopoietin: master switch for allergic inflammation" *JEM*, Feb. 20, 2006, pp. 269-273, vol. 203, No. 2.
Remaut, E. et al. "Clinical Potential of *Lactococcus lactis* Mediated Delivery of Human Interleukin-10 and Trefoil Factors" *Bioscience Microflora*, Aug. 1, 2006, pp. 81-97, vol. 25, No. 3.
Spadoni, I. et al. "Dendritic cells produce TSLP that limits the differentiation of Th17 cells, fosters Treg development, and protects against colitis" *Mucosal Immunology*, Mar. 2012, pp. 184-193, vol. 5, No. 2.
Taylor, B. C. et al. "TSLP regulates intestinal immunity and inflammation in mouse models of helminth infection and colitis" *JEM*, Mar. 9, 2009, pp. 655-667, vol. 206, No. 3.
Written Opinion in International Application No. PCT/EP2016/058020, dated Aug. 9, 2016, pp. 1-10.

* cited by examiner

*Primary Examiner* — Brian Gangle
(74) *Attorney, Agent, or Firm* — Saliwanchik, Lloyd & Eisenschenk

(57) ABSTRACT

The present invention relates to recombinant *Lactococcus lactis* bacteria expressing and secreting TSLP or IL-25 or a combination thereof, and their use as probiotics or therapeutic agents, especially for use in the treatment of inflammatory diseases and disorders.

8 Claims, 16 Drawing Sheets

Specification includes a Sequence Listing.

LACTOCOCCUS LACTIS PRODUCING TSLP OR IL-25 AND THEIR USES AS PROBIOTICS AND THERAPEUTICS

CROSS-REFERENCE TO RELATED APPLICATION

This application is the U.S. national stage application of International Patent Application No. PCT/EP2016/058020, filed Apr. 12, 2016.

The Sequence Listing for this application is labeled "Seq-List.txt" which was created on Oct. 12, 2017, and is 6 KB. The entire content of the sequence listing is incorporated herein by reference in its entirety.

FIELD OF THE INVENTION

The present application relates to the microbiology and medicine field. More particularly, it relates to a recombinant bacterium producing a cytokine for use as therapeutics, in particular as anti-inflammatory agent.

BACKGROUND OF THE INVENTION

Inflammatory Bowel disease (IBD) which gathers Crohn's disease (CD) and Ulcerative Colitis (UC) affects 1.4 million Americans and the prevalence rate is 396 per 100 000 individuals worldwide. Incidence and prevalence are increasing in various regions of the world including the ones which were less impacted.

Due to its symptoms (diarrhea, abdominal pain, loss of weigh), IBD is considered as an incapacitating disease. Patients have a higher risk factor to develop other inflammatory or non-inflammatory disorders like psoriasis, cancer or arthritis. So far no curative treatments exist for the disease. The most powerful treatment is the injection of the recombinant antibodies targeting TNF-α (infliximab), however even if 60% are primary responders this drops to 25-40% still in remission after one year of treatment. The last solution in IBD is surgery where inflamed parts of the intestine are withdrawn. However surgery can lead to severe complications as Short Bowel syndrome and relapses are frequent. All together, this makes IBD one of the major health problems in developed country and the development of innovative therapeutics or curative strategies is crucial.

One of the ways explored to help in alleviating symptoms of the disease is the delivery of anti-inflammatory molecules by recombinant lactic acid bacteria (LAB). Recently, it has been shown that mice fed with LAB expressing the protease inhibitor Elafin were protected against gut inflammation. LAB have been used for thousand years for food conservation and appear to be a promising vehicle delivering active molecules. They are recognized as safe by World Health Organization, and some strains can have anti-inflammatory properties.

*Lactococcus lactis* is the most widely used Lactic Acid Bacterium (LAB) in the production of fermented milk products and is considered as the model LAB because many genetic tools have been developed and its complete genome has been completely sequenced (Bolotin, Wincker et al. 2001, Genome Res, 11, 731-753). Thus, this food-grade Gram-positive bacterium represents a good candidate to produce and deliver therapeutic proteins to the mucosal immune system. In the last decade, the potential of live recombinant lactococci to deliver such proteins to the mucosal immune system has been widely investigated (Steidler, Robinson et al. 1998, Infect Immun, 66, 3183-3189; Bermudez-Humaran, Cortes-Perez et al. 2004, J Med Microbiol, 53, 427-433; Hanniffy, Wiedermann et al. 2004, Adv Appl Microbiol, 56, 1-64; Wells and Mercenier 2008, Nat Rev Microbiol, 6, 349-362; Bermudez-Humaran, Kharrat et al. 2011, Microb Cell Fact, 10 suppl 1, S4). This approach offers several advantages over the traditional systemic injection, such as easy administration and the ability to elicit both systemic and mucosal immune responses (Mielcarek, Alonso et al. 2001, Adv Drug Deliv Rev, 51, 55-69; Eriksson and Holmgren 2002, Curr Opin Immunol, 14, 666-672).

Initial studies on the use of *L. lactis* secreting biologically active molecules were performed with murine interleukin-2 (IL-2, a pro-inflammatory cytokine) (Steidler, Robinson et al. 1998, supra). The encouraging data obtained in this pioneer work stimulated researchers to further investigate whether mucosal and systemic responses could be enhanced by co-expression (and secretion) of either muIL-2 or muIL-6 (another pro-inflammatory cytokine) with the model antigen Tetanus Toxin Fragment C (TTFC) (Steidler, Robinson et al. 1998, supra). Compared to mice immunized with a TTFC-expressing strain of *L. lactis*, the anti-TTFC serum responses peak was 10-15-fold higher in mice co-immunized with the TTFC-expressing *L. lactis* strain and *L. lactis* expressing either muIL-2 or muIL-6. This was the first demonstration that biologically active cytokines could be delivered to the mucosa using LAB. Then, the laboratory reported a *L. lactis* strain able to deliver in situ biologically active muIL-12 (LL-muIL12) at mucosal surfaces (eg. airway or digestive mucosa). IL-12 is a potent pleiotropic cytokine that induces T helper 1 ($T_H1$) cells and interferon-γ (IFN-γ) production, enhances cytotoxic T lymphocyte (CTL) maturation, promotes natural killer (NK) cell activity and possesses adjuvant properties when co-delivered with vaccinal antigens. Particularly, we used 3 models where LL-muIl-12 was successfully used: (1) as an adjuvant in the context of mucosal vaccination against Human Papillomavirus type-16 (HPV-16) (Bermudez-Humaran, Langella et al. 2003, Infect Immun, 71, 1887-1896; Bermudez-Humaran, Cortes-Perez et al. 2004, supra; Adel-Patient, Ah-Leung et al. 2005, Cin Exp Allergy, 35, 539-546), (2) to modulate $T_H1/T_H2$ balance in an ovalbumin (OVA)-induced asthma model (Wu, Yang et al. 2006, Int Immunopharmacol 6, 610-615) and (3) to prevent an allergic reaction against the cow's milk allergen β-lactoglobulin (BLG) (Adel-Patient, Ah-Leung et al. 2005, supra; Cortes-Perez, Ah-Leung et al. 2007, Clin Vaccine Immunol 14, 226-233).

However, there is still a strong need of new LAB which could be used as anti-inflammatory agent.

SUMMARY OF THE INVENTION

The present invention relates to a recombinant *Lactococcus lactis* bacterium expressing either interleukin 25 (IL-25) or Thymic Stromal LymphoPoietin (TSLP), using for instance a Stress-Induced Controlled System (SICE) expression system. The recombinant *Lactococcus lactis* bacteria as disclosed herein are able to express and secrete efficiently both cytokines in a biologically active form. The inventors showed that the recombinant *Lactococcus lactis* bacterium expressing either IL-25 (LL-IL-25) or TSLP (LL-TSLP) is able to diminish the inflammation.

Therefore, the present invention relates to a recombinant *Lactococcus lactis* bacterium, wherein the bacterium comprises an expression cassette comprising a heterologous nucleotide sequence encoding a cytokine selected from the group consisting of thymic stromal lymphopoietin (TSLP) and interleukin-25 (IL-25). The heterologous nucleotide sequence can be expressed under the control of a promoter of the GroESL operon of *Lactococcus lactis*. Preferably, the expression cassette further comprises a nucleotide sequence encoding an extracellular addressing peptide, especially the peptide signal of Exp4 protein of *Lactococcus lactis*. More preferably TSLP or IL-25 is human.

The present invention further relates to the recombinant *Lactococcus lactis* bacterium as disclosed herein for use as a probiotic or as an anti-inflammatory agent.

In addition, the present invention relates to a pharmaceutical, veterinary or probiotic composition comprising a recombinant *Lactococcus lactis* bacterium as disclosed herein. In an embodiment, the composition comprises a recombinant *Lactococcus lactis* bacterium capable of secreting TLSP and/or a recombinant *Lactococcus lactis* bacterium capable of secreting IL-25. Optionally, the composition may further comprise an additional active ingredient, for example a drug such as an anti-inflammatory or immunemodulatory drug.

The present invention relates to a food composition comprising a recombinant *Lactococcus lactis* bacterium as disclosed herein or a combination thereof, preferably a diary product.

Finally, the present invention relates to a recombinant *Lactococcus lactis* bacterium as disclosed herein or a combination thereof for use for the prophylaxis or treatment of an inflammatory condition. It also relates to the use of a recombinant *Lactococcus lactis* bacterium as disclosed herein or a combination thereof for the manufacture of a medicament for the treatment of an inflammatory condition. It relates to a method for treating an inflammatory condition in a subject in need thereof comprising administering a therapeutically effective amount of a recombinant *Lactococcus lactis* bacterium as disclosed herein or a combination thereof. Preferably, the inflammatory condition is an intestinal inflammatory condition such as one selected from the group consisting of inflammatory bowel disease, Crohn's disease, ulcerative colitis, chronic colitis, diversion colitis, pouchitis, necrotizing enterocolitis, and irritable bowel syndrome. Preferably, the recombinant *Lactococcus lactis* bacterium is intended for oral administration. In a preferred embodiment, the recombinant *Lactococcus lactis* bacterium is intended to be administered in the early phase of inflammation. Preferably, the recombinant *Lactococcus lactis* bacterium is intended to be administered once or twice a day during a period of less than a week.

DETAILED DESCRIPTION OF THE INVENTION

Figure 1:
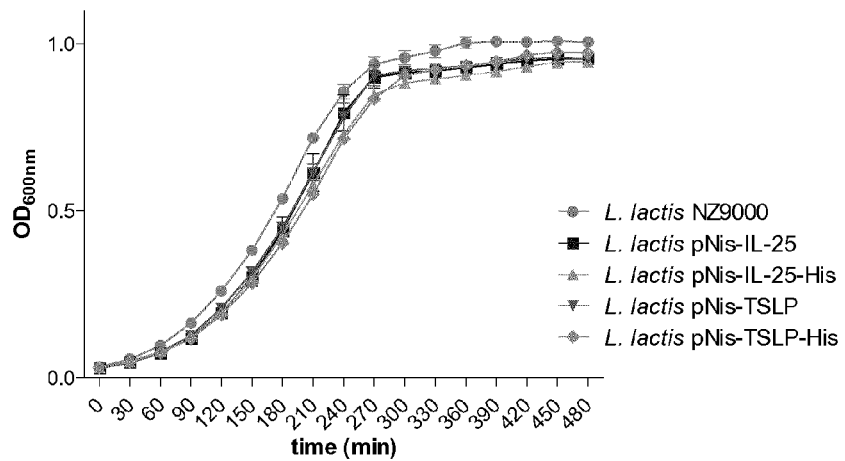
FIG. 1: Bacterial growth curves of *L. lactis* wild type (NZ9000), *L. lactis* pNis-IL-25, *L. lactis* pNis-IL25-His, *L. lactis* pNis-TSLP and *L. lactis* pNis-TSLP-His in M17 medium supplemented with 0.5% glucose and 10 µg/mL chloramphenicol for strains containing plasmid.

In a first object, the present invention relates to a recombinant or genetically-engineered *Lactococcus lactis* bacterium comprising a heterologous nucleotide sequence encoding a cytokine selected in the group consisting of thymic stromal lymphopoietin (TSLP) and interleukin-25 (IL-25). The *Lactococcus lactis* bacterium is a good-grade bacterium, thereby possessing a perfect safety profile recognized by the GRAS (Generally Recognized As Safe) and QPS (Qualified Presumption of Safety) status in USA and European Community, respectively. Such bacterium can be safely in functional foods or food additives with allegations concerning maintain in good health and well-being or prevention of disease.

Preferably, the *Lactococcus lactis* bacterium is prepared from a bacterium selected among *Lactococcus lactis* subsp. *cremoris* (including A76, GE214, HP, IBB477, KW2, MG1363, HB60, HB61, HB63, NBRC 100676, NZ9000, SK11, TIFN1, TIFN3, TIFN5, TIFN6, TIFN7, DSM14797, CNCM I-2807, DN030066 (CNCM I-1631), DN030087 (CNCM I-2807), CNCM I-1631, NCC2287 (CNCM I-4157) or UC509.9), *Lactococcus lactis* subsp. *lactis* (including 1AA59, A12, CNCM I-1631, CV56, Delphy 1, Il1403, IO-1, DPC3901, LD61, TIFN2, TIFN4, JCM 5805 also called NBRC 100933, JCM 7638, K214, KF147, KLDS 4.0325, NCDO 2118 or YF11), *Lactococcus lactis* subsp. *hordniae* (such as NBRC 100931) or *Lactococcus lactis* subsp. *tructae*. Preferably, the *Lactococcus lactis* bacterium is selected from *Lactococcus lactis* subsp. *cremoris* and *Lactococcus lactis* subsp. *lactis*, especially *Lactococcus lactis* subsp. *lactis* bv. *Diacetylactis*.

In a particular embodiment, the *Lactococcus lactis* bacterium is prepared from *Lactococcus lactis* subsp. *Cremoris*, preferably MG1363 (GenBank NC_009004).

The recombinant or genetically-engineered *Lactococcus lactis* bacterium of the invention is capable of expressing and secreting a cytokine selected in the group consisting of TSLP and IL-25. Therefore, the bacterium comprises an expression cassette comprising a nucleotide sequence encoding the cytokine. The nucleotide sequence expressing the cytokine can be under the control of the promoter of the GroESL operon of *Lactococcus lactis*. Such expression system has been disclosed in detail in WO 2013/175358, the disclosure of which being incorporated herein by reference. In particular, the promoter sequence can be selected among a sequence disclosed in any one of SEQ ID Nos 1-4, preferably of SEQ ID No 1, or a sequence having at least 90%, 95%, or 99% of identity with one of these sequences.

By "heterologous nucleotide sequence encoding a cytokine" is meant that either the nucleotide sequence is not a sequence naturally occurring in *Lactococcus lactis* and/or the sequence is not found naturally operationally linked to the promoter of the GroESL operon of *Lactococcus lactis*. In a first aspect, the cytokine is TSLP (Homologene: 81957). Preferably, the cytokine is the human TSLP disclosed in the reference databases: HGNC: 30743; Entrez Gene: 85480; UniProtKB: Q969D9; NP_149024; NM_033035. The amino acid sequence of human TSLP is shown in SEQ ID No 5. Optionally, the encoded TSLP can be the TSLP devoid of its signal peptide. For instance, in human TSLP, the signal peptide is located at position 1-29 of SEQ ID No 5. Therefore, the encoded TSLP can be the amino acid sequence starting at position 30 up to the end of SEQ ID No 5. For expression in bacteria, the signal peptide can be replaced by a Methionine. Alternatively, if veterinary use is contemplated, then the TSLP sequence of the animal to be treated will be used. Optionally, TSLP may include TSLP variants having some modifications such as substitution, deletion or addition of 1-10 amino acids or such as truncation. Examples of variants are disclosed in WO2002/00724.

In a second aspect, the cytokine is IL-25 (Homologene: 15429). Preferably, the cytokine is the human IL-25 disclosed in the reference databases: HGNC: 13765; Entrez Gene: 64806; UniProtKB: Q9H293; NP_073626; NM_022789. The amino acid sequence of human TSLP is shown in SEQ ID No 6. Optionally, the encoded IL-25 can be the IL-25 devoid of its signal peptide. For instance, in human IL-25, the signal peptide is located at position 1-32. Therefore, the encoded IL-25 can be the amino acid sequence starting at position 33 up to the end of SEQ ID No 6. In addition, the encoded IL-25 can be the isoform 2 in which residues 1-18 are replaced by MY (as shown in SEQ ID No 7). For expression in bacteria, the signal peptide can be replaced by a Methionine. Alternatively, if veterinary use is contemplated, then the IL-25 sequence of the animal to be treated will be used. Optionally, IL-25 may include IL-25 variants having some modifications such as substitution, deletion or addition of 1-10 amino acids or such as truncation.

The nucleotide sequence encoding a cytokine can use any suitable genetic code and can be the naturally occurring coding sequence. Alternatively, the coding sequence can be optimized for the *Lactococcus lactis* bacterium.

In addition, the expression cassette preferably further comprises a nucleotide sequence encoding an extracellular addressing peptide. For instance, the extracellular addressing peptide can be the signal peptide of Exp4 protein of *Lactococcus lactis*, especially as disclosed in SEQ ID No 8. The nucleotide sequence encoding the extracellular addressing peptide is operationally linked to the sequence encoding the cytokine so as to lead to the production of a protein fusion including the extracellular addressing peptide and the cytokine. Optionally, the extracellular addressing peptide can substitute the signal peptide of the cytokine or can be just added to the cytokine.

The expression cassette encoding the cytokine can be integrated into the *Lactococcus lactis* chromosome or can be kept in an episomal form (i.e., in a plasmid).

Optionally, the recombinant *Lactococcus lactis* bacterium may comprise two expression cassettes, one for TSLP and the other for IL-25, or an expression cassette expressing both cytokines.

The recombinant *Lactococcus lactis* bacterium is obtained by introducing the expression cassette as disclosed above in a *Lactococcus lactis* bacterium, especially one disclosed above.

In a particular embodiment, the recombinant *Lactococcus lactis* bacterium is one of the two strain deposited at the CNCM (Collection Nationale de Culture de Miroorganismes), 25 rue du Docteur Roux, 75724 Paris, Cedex 15, France, on Apr. 14, 2015 under deposit number CNCM I-4971 (for IL-25) and I-4972 (for TSLP). In addition, the recombinant *Lactococcus lactis* bacterium can be prepared by substituting in one of these strains the murine sequence by the human sequence of the cytokine.

The present invention also relates to the use of a recombinant *Lactococcus lactis* as disclosed above as probiotic. Accordingly, it can be used for preventing inflammation, in particular intestinal inflammation, in a healthy subject. The present invention relates to a food composition comprising a recombinant *Lactococcus lactis* producing TSLP, a recombinant *Lactococcus lactis* producing IL-25, a recombinant *Lactococcus lactis* producing both TSLP and IL-25 or the combination of a recombinant *Lactococcus lactis* producing TSLP and a recombinant *Lactococcus lactis* producing IL-25.

Alternatively, the recombinant *Lactococcus lactis* bacterium of the present invention can be for use as a drug, especially as an anti-inflammatory agent.

The present invention relates to a pharmaceutical or veterinary composition. The composition according to the invention may comprise a recombinant *Lactococcus lactis* producing TSLP, a recombinant *Lactococcus lactis* producing IL-25, a recombinant *Lactococcus lactis* producing both TSLP and IL-25 or the combination of a recombinant *Lactococcus lactis* producing TSLP and a recombinant *Lactococcus lactis* producing IL-25. Preferably, the composition comprises an efficient amount of bacteria, in particular a therapeutically effective amount of bacteria. In particular, a therapeutically effective amount is so that the inflammatory state is prevented or cured, the progression of inflammation is slow-down or blocked, and/or the inflammatory symptoms are alleviated. For instance, the composition contains at least $1 \times 10^6$ colony-forming units (CFU) of bacteria, preferably at least $1 \times 10^7$ CFU, more preferably at least $1 \times 10^8$ CFU, for instance between $1 \times 10^7$ CFU and $1 \times 10^{11}$ CFU.

Optionally, the composition may further comprise an additional active ingredient. The additional active ingredient can be another bacterium. The additional active ingredient can also be a drug, such as an anti-inflammatory agent, an immune-modulatory agent, and the like. More specifically and non-exhaustively, the additional drug could be selected among corticosteroid, sulphasalazine, derivative of sulphasalazine, immunosuppressive drug, cyclosporin A, mercaptopurine, azathioprine, an antibiotic, cytokine or cytokine antagonist such as tumor necrosis factor-α antagonist, IL-10, IL-27, or IL-35.

The present invention relates to a recombinant *Lactococcus lactis* bacterium according to the present invention or a pharmaceutical composition as disclosed above for use for the prophylaxis or treatment of an inflammatory condition. The inflammatory disorder can be selected from the group consisting of acute inflammations such as sepsis; burns; and chronic inflammation. The inflammatory disorder can be an inflammatory condition of the intestine (e.g., including celiac disease, diverticulitis and appendicitis), stomach, liver, pancreas or peritoneum or other tissue of the gastrointestinal tract or digestive system. Such other conditions can include inflammatory conditions of the oral cavity, esophagus, pancreas, pancreatic duct, liver, gallbladder, duodenum, bile duct, small intestine (ileum), large intestine (colon), caecum, appendix, or rectum. Specific conditions affecting the gastrointestinal system that may be treatable by the methods, compositions and kits of the present invention can include, for example, diverticulitis (a common digestive disease particularly found in the large intestine which develops from diverticulosis and involves the formation of inflamed pouches (diverticula) on the outside of the colon), celiac disease (an autoimmune disorder of the small intestine that occurs in genetically predisposed people of all ages from middle infancy onward caused by an autoimmune reaction that develops against gluten protein), appendicitis (condition characterized by inflammation of the appendix), gastroenteritis (inflammation of the gastrointestinal tract, involving both the stomach and the small intestine and resulting in acute diarrhea and which is caused most often by an infection from certain viruses or less often by bacteria, their toxins, parasites, or an adverse reaction to something in the diet or medication), pancreatitis (chronic or acute inflammation of the pancreas due to various causes), or peptic ulcer disease.

In a preferred embodiment, the inflammatory disorder is selected among inflammatory bowel disease, Crohn's disease, ulcerative colitis, chronic colitis, diversion colitis, pouchitis; necrotizing enterocolitis; and irritable bowel syndrome; skin inflammation, such as UV or chemical-induced skin inflammation, eczema, reactive skin; eye inflammation; allergy, asthma; obesity-associated inflammation; age-related low-grade inflammation, and combinations thereof. The inflammatory disorder can also be an inflammatory condition of an inflammatory pulmonary disease, Inflammatory articular disease and Inflammatory urogenital disease. Inflammatory pulmonary diseases include cystic fibrosis, asthma and COPD (chronic obstructive pulmonary disease).

As used herein, the term "treatment" or "treating" includes any process, action, application, therapy, or the like, wherein a subject (or patient), including a human being, is provided with or administered an agent or composition (or recombinant organism expressing the agent of the invention) with the aim of improving the subject's condition, directly or indirectly, or slowing the progression of a condition or disorder in the subject, or ameliorating at least one symptom of the disease or disorder under treatment.

The composition of the present invention may be any kind of composition. The composition may be administered orally, enterally, intra-vaginally, intra-rectally, topically or ocularly, for example. For example it may be a pharmaceutical composition, a nutraceutical, a food additive, a cosmetical composition, a pet food, a food product, or a drink.

The composition according to the invention is preferably intended for oral administration. For example, compositions can be in the form of a suspension, tablet, pill, capsule or powder. Optionally, it can be in the form of a beverage, e.g. a diary or non-diary beverage.

Alternatively, the composition according to the invention is intended for rectal administration. The rectal administration can take place in the form of a suppository, enema or foam.

The subject to be treated is preferably a mammal, especially a human. It can be an infant, a child, an adult or the elderly.

The composition of the present invention can be administered once, twice, three times or four times a day. Preferably, it is administered once or twice a day, more preferably once. In addition, it can be administered every day, every two days, every three days, or once or twice a week. The treatment period can be short or long. By a short period, is intended no more than a week, for instance 3, 4, 5 or 6 days. By a long period, is intended a period of more than one week, for instance 2, 3 or 4 weeks. In a preferred embodiment, the composition is administered once or twice a day during a period of less than a week. The composition can be administered during several periods, preferably with a rest period between two periods of treatments.

The composition can be administered as a prophylactic treatment, i.e. before the occurrence of an inflammatory event. Alternatively, it can be administered in the early phase of the inflammation, for instance as soon as the first symptom(s) appear(s). In addition, it can also be administered during the acute phase of the inflammation. Finally, it can be administered during the recovering phase after the inflammation. It can also be administered during a combination of those phases. In a preferred embodiment, it can be administered in the early phase of the inflammation once or twice a day during a period of less than a week.

The above disclosure generally describes the present invention. A more complete understanding can be obtained by reference to the following specific examples, which are provided for purposes of illustration only and are not intended to limit the scope of the invention.

EXAMPLES

Summary

IL-25 and TSLP are two cytokines mainly secreted by epithelial cells that are involved in T helper 2 (Th2) responses. In order to test the impact of these two cytokines in chemical-induced murine colitis models, several recombinant lactic acid bacteria (LAB) were constructed.

The inventors have constructed different recombinant strains of *Lactococcus lactis* and *Lactobacillus casei* (two well-known LAB strains) expressing either interleukin 25 (IL-25) and Thymic Stromal LymphoPoietin (TSLP) cytokines using two different expression systems: the Nisin-Induced Controlled System (NICE) and the Stress-Induced Controlled System (SICE). In addition, they have also constructed recombinant LAB strains expressing a His-tagged form of these two cytokines.

Once confirmed the correct growth of recombinant LAB, the inventors tested IL-25 and TSLP production and secretion by Western blot and ELISA using the two different expression systems with their corresponding stress. Their results showed that recombinant LAB can express both cytokines using the two expression systems (ie. NICE and SICE), although no secretion was observed with the NICE system in the tested conditions. Concerning the SICE system, a good secretion was only observed in recombinant *L. lactis* strains. Furthermore, they demonstrated that cytokine secretion is increased in these strains after either a saline or heat shock stress. Moreover, they showed a biological activity of these cytokines secreted by recombinant *L. lactis*.

Then, the inventors evaluated the immuno-modulatory and prophylactic effects of recombinant LAB strains expressing IL-25 and/or TSLP in vivo. They chose 2 recombinant *L. lactis* expressing either IL-25 or TSLP under the SICE expression system that presented the higher cytokine secretion. Different chemical-induced murine colitis models were tested in the inventors' laboratory in order to determine the prophylactic and immunomodulatory effects of the strains. First, they showed that LL-TSLP is able to diminish the inflammation in the intestine and thus to protect mice from a DSS-induced acute colitis. Daily LL-TSLP force-feeding delayed clinical signs (feces softening and bleeding) at the beginning of the colitis. More important, LL-TSLP protects intestinal epithelium from damages induced by chemical treatment due to a decrease of histological score. Furthermore, TSLP-secreted by recombinant *L. lactis* was able to reduce pro-inflammatory cytokine (IFN-γ) production, and diminish the pro-inflammatory Th17 response, showing that secreted TSLP modulates inflammation.

The inventors also performed a DSS-induced colitis followed by 5 days of recovery. In this model, they observed a decrease of several inflammation markers after LL-TSLP treatment such as diminution of MPO activity (reflecting a less granulocytes recruitment), a smaller thickening of the colonic wall, and a diminution of the pro-inflammatory cytokine IL-12 in colonic tissue. Moreover, they showed that LL-TSLP was able to decrease pro-inflammatory Th17 response induced by DSS and to enhance the important inflammation regulation pathway: the $T_{reg}$ response. These results seems to describe an anti-inflammatory role of LL-TSLP.

On the other hand, the inventors demonstrated that IL-25 secreting *L. lactis* was able to drive a Th2 response in a DSS-induced acute colitis but this response was not sufficient to protect mice from inflammation. As the same time, they used a DNBS-induced acute colitis, known to drive a Th1 inflammation. They observed a protective role of IL-25 by a decrease of the mortality of mice, a lower weight loss and a smaller thickening of colonic tissue, suggesting an important role of IL-25-secreting *L. lactis* in the diminution of intestinal inflammation.

Example 1

Construction of Recombinant LAB Expressing muIL-25 and muTSLP

Thymic Stromal Lymphopoietin (TSLP) and IL-25 are two cytokines produced by epithelial cells. Both cytokines initiate $T_H2$ type immune responses including the secretion of IL-4 and IL-13 (two anti-inflammatory cytokines) by basophils and $T_H2$ cells.

By activating the production of anti-inflammatory IL-4 and IL-13 cytokines and inhibiting the production of pro-inflammatory IL-12, the inventors expected that delivery of TSLP and/or IL-25 at the mucosal level by recombinant LAB would modulate the immune response toward an anti-inflammatory immune profile. This hypothesis has been validated after construction and characterization of recombinant LAB expressing IL-25 or TSLP.

The inventors have successfully constructed 16 recombinant *L. lactis* and *L. casei* strains expressing either IL-25 or TSLP cytokines. Two inducible expression systems, the Nisin-Induced Controlled System: NICE, and a Stress-Induced Controlled System: SICE (Benbouziane, Ribelles et al. J Biotechnol, 168, 120-129) were used to achieve IL-25 and TSLP expression and two different forms of each protein were produced: a native and a His-tagged form. Once confirmed the correct growth of recombinant LAB (ie. *L. lactis* and *L. casei* BL23), the inventors tested IL-25 and TSLP production and secretion by both Western blot and ELISA using the two different expression systems with their corresponding inductors, nisin for the NICE system and stress for SICE system. Although their results showed that recombinant LAB are able to express both cytokines using the two expression systems, no cytokine secretion was observed with the NICE system in the tested conditions. Concerning the SICE system, a good secretion was only observed with recombinant *L. lactis* strains.

Materials & Methods

Bacterial Strains and Growth Conditions

The bacterial strains and plasmids used in the present work are listed in Table 1. *L. lactis* strains were grown in M17 medium (Difco) supplemented with 1% glucose at 30° C. without agitation. *L. casei* strains were grown in MRS medium (Difco) at 37° C. without agitation. *Escherichia coli* strains were grown in Luria-Bertani (Difco) at 37° C. and 180 rpm. Plasmids were selected by addition of antibiotics as follows (concentrations in milligrams per milliliter): for *L. lactis* chloramphenicol (10); for *E. coli*, ampicillin (100) and chloramphenicol (10).

Two different bacterial growth curves were realized.

Overnight cultures of cytokine-secreting LAB strains were diluted at optical density at 600 nm ($OD_{600\,nm}$)=0.1. Stress was then induced and 100 µL of each bacterial culture were seeded into sterile 96 well-plates. These plates were incubated for 20 h to 30° C. (*L. lactis*) or 37° C. (*L. casei*) in microplate photo-spectrometer (TECAN). $OD_{600\,nm}$ was measured every 15 min, after orbital shaking during 15 sec.

During stress inducing secretion assays, $OD_{600\,nm}$ of the different bacterial strains were measured at various time points (see materials and methods, Stress inducing cytokine secretion by LAB).

Construction of Recombinant LAB Strains

Plasmid DNA isolation and general procedures for DNA manipulations follow the commercial protocol of used kits (Qiagen, Promega).

NICE System

*L. lactis* pNis-cytokine

Plasmids containing either murine IL-25, His-tagged murine IL-25 (6 His residues at C-Term), murine TSLP or His-tagged murine TSLP (6 His residues at C-Term) were synthesized by Geneart (Invitrogen). These plasmids harbor the ampicillin resistance gene. After digestion by SpeI and NsiI, the fragment containing the gene of interest (murine IL-25, IL-25-His, TSLP or TSLP-His) was integrated in a SpeI/NsiI-digested pNis plasmid. Constructions were established by electroporarion into *L. lactis* NZ9000 strain at 2.4 KV, 200 □, 25 ρF. Transformants were then selected at 30° C. on M17 agar containing 1% glucose and chloramphenicol (10 µg/mL). Plasmids were extracted from recombinant transformants and verified by digestion and sequencing, and named pNis-IL-25, pNis-IL-25-His, pNis-TSLP and pNis-TSLP-His.

*L. casei* pNis-cytokine pNis-IL-25, pNis-IL-25-His, pNis-TSLP and pNis-TSLP-His plasmids were extracted from *L. lactis* and electroporated into *L. casei* nisRK at 1.5 KV, 400 □, 25 µF. Transformants were selected at 37° C. on MRS agar containing chloramphenicol (10 µg/mL). Plasmids were extracted from recombinant transformants and verified by digestion and sequencing.

SICE System

*L. lactis* pGroEL-cytokine pNis-IL-25, pNis-IL-25-His, pNis-TSLP and pNis-TSLP-His were digested by BamHI and SpeI. After digestion, the fragment containing the gene of interest (murine IL-25, IL-25-His, TSLP or TSLP-His) was integrated into BamHI/SpeI digested pGroEL plasmid. Constructions were established by electroporation into *L. casei* BL23 at 1.5 KV, 400 □, 25 µF. Transformants were selected at 37° C. on MRS agar containing chloramphenicol (10 µg/mL). Plasmids were extracted from transformants and verified by digestion and sequencing, and named pGroEL-IL-25, pGroEL-IL-25-His, pGroEL-TSLP and pGroEL-TSLP-His.

*L. casei* pDnaK-cytokine pMA-pdnaK-SPp40 plasmid (synthesized by Geneart, Invitrogen) was digested by BglII and NsiI. After digestion, the fragment containing the promoter from dnaK gene and the peptide signal of P40 protein (a well-secreted protein in *L. casei* BL23) was integrated into BglII/NsiI digested pNis-IL-25, pNis-IL-25-His, pNis-TSLP, pNis-TSLP-His or pNis-Nuc plasmids. Constructions were established by electroporation into *L. lactis* MG1363 at 2,400 V, 200 Ω, 25 µF. Transformants were selected at 30° C. on M17 agar containing 1% glucose and chloramphenicol (10 µg/mL). Plasmids were extracted from transformants and verified by digestion and sequencing, and named pDnaK-IL-25, pDnaK-IL-25-His, pDnaK-TSLP, pDnaK-TSLP-His and pDnaK-Nuc.

Nisin Inducing Cytokine Secretion by LAB

*L. lactis* pNis-cytokine

Overnight cultures of cytokine secreting *L. lactis* strains were diluted in M17 medium supplemented with 1% glucose and 10 µg/mL chloramphenicol to a 0.1 $OD_{600\,nm}$ and incubated at 30° C. without agitation until a 0.4-0.6 $OD_{600\,nm}$. Then the nisin (Sigma) was added to various concentrations: 0, 1 and 10 ng/mL and incubate at 30° C. without agitation. At different times (T30 min, T5 h and T24 h), 1 mL of bacterial cultures were harvested and centrifuged at 4° C. and 10 000 rpm during 10 min. The 2 µm filtered supernatants were conserved at −20° C. for cytokine quantification by ELISA.

*L. casei* pNis-cytokine

The protocol used was identical to that used for *L. lactis* but with the specific-growth conditions of *L. casei*.

Stress Inducing Cytokine Secretion by LAB

Overnight cultures of cytokine-secreting *L. lactis* strains were diluted in M17 medium supplemented with 1% glucose and 10 µg/mL chloramphenicol to a 0.1 $OD_{600\,nm}$ and incubate at 30° C. without agitation until a 0.4-0.6 $OD_{600\,nm}$. Then different stresses were added as following.

Salt Stress

Different volumes of NaCl 5M solution were added into culture to obtain 0, 1, 1.5, 2, 2.5, 3 and 3.5% NaCl final concentration (corresponding to T0) and incubate at 30° C. without agitation. At various time (T30 min, T4 h or T5 h and T24 h), 1 mL of bacterial cultures were harvested and centrifuged at 4° C. and 10 000 rpm during 10 min. The 2 µm filtered supernatants were conserved at −20° C. for cytokine quantification by ELISA.

Heat-shock

Bacterial cultures were centrifuged at room temperature and 4700 rpm during 15 min. Pellets were resuspended with pre-warmed culture medium at 30° C., 37° C., 40° C. or 43° C. (corresponding to T0) and incubate at these different temperatures without agitation. At various time (T30 min, T4 h and T24 h), 1 mL of bacterial cultures were harvested and centrifuged at 4° C. and 10 000 rpm during 10 min. The 2 µm filtered supernatants were conserved at −20° C. for cytokine quantification by ELISA.

Acidic pH Stress

Bacterial cultures were centrifuged at room temperature and 4700 rpm during 15 min. Pellets were resuspended with culture medium at pH 7 or pH 5.4 (corresponding to T0) and incubate at these different pH, 30° C. and without agitation. At various time (T30 min, T4 h and T24 h), 1 mL of bacterial cultures were harvested and centrifuged at 4° C. and 10 000 rpm during 10 min. The 2 µm filtered supernatants were conserved at −20° C. for cytokine quantification by ELISA.

Western Blot Analysis

To quantify IL-25-His, protein samples were prepared from 2 mL of induced or non-induced cultures. After centrifugation (10 min, 10 000 rpm and 4° C.), the cell pellet and the supernatant were treated separately. The supernatants were treated with 200 µL of 100% trichloroacetic acid (sigma) during 2 h at 4° C. to precipitate proteins. These ones were recovered from the pellets after centrifugation at 4° C. for 20 min at 13 000 rpm. The cell fraction was obtained by cell disruption by 5 cycles of 10 sec of sonication. Western blotting was performed with samples corresponding to equal number of bacteria, a His-tagged protein as positive control and using a rabbit anti-His-Tag (Sigma) and a goat anti-rabbit (P.A.R.I.S. Anticorps).

Concentration of Cytokines

The concentration of cytokines was performed from 88 mL of *L. lactis* pGroEL-TSLP overnight culture and 80 mL of *L. lactis* pGroEL-IL-25 overnight culture, both induced with 2.5% of NaCl and using a centricon Plus-70 centrifugal Filter unit (10 000 NMWL). The concentrated solution was quantified by ELISA: 1.58 µg/mL (KIT eBiosciences) or 22 µg/mL (KIT R&D systems) for IL-25 and 0, 485 µg/mL for TSLP. For each concentration, a negative control of the bacterial culture medium was prepared using *L. lactis* strain harboring a plasmid encoding for a non-relevant protein, the nuclease Nuc (*L. lactis* pGroEL-Nuc).

Isolation and Culture of Bone Marrow-Derived Dendritic Cells

Bone marrow cells from BALB/c mice were harvested aseptically and plated into petri dish in RPMI 1640 (Life Technologies) supplemented with 10% decomplemented FBS, penicillin/streptomycin, β-mercaptoethanol 5 mM and 20 ng/mL GM-CSF (peprotech). 15 mL of medium was added at day 3 and completely changed at day 5; cells were harvest at day 7. Bone marrow dentritic cells (BMDCs) were then plated at $5 \times 10^5$ cells/well (96 wells/plate) and cultured in RPMI 1640 supplemented with 10% decomplemented fetal bovine serum (FBS) and penicillin/streptomycin at 37° C. in a 10% $CO_2$ humidified incubator.

TSLP Activity Test: LPS-Stimulated-BMDC Assays

BMDCs were stimulated with LPS (unstimulated or 5 ng/mL) and with concentrated rTSLP at various concentrations. Commercial TSLP was added at 0, 5, 10, 50 and 100 ng/mL (Biolegend) and concentrated rTSLP at 5 and 10 ng/mL. A negative control of the culture medium (filtered supernatant of *L. lactis* pGroEL-Nuc) was used and equivalent protein amount corresponding to concentrations used with concentrated rTSLP was added. 24 h after stimulation, cells supernatant were harvested for IL-12 quantification by ELISA.

Isolation and Culture of Splenocytes

Spleens were removed aseptically from BALB/c mice and grinded in RPMI 1640 (Life Technologies) to generate single-cell suspensions. Erythrocytes were lysed with a Red Cell Lysis Buffer (Sigma). Splenocytes were cultured in RPMI 1640 supplemented with decomplemented FBS 10% and penicillin/streptomycin at 37° C. in a 10% $CO_2$ humidified incubator at $5 \times 10^6$ cells/wells (24 wells/plate).

IL-25 Activity Test: Splenocytes Assays

Splenocytes were stimulated with commercial IL-25 (unstimulated, 1, 2.5, 5, 10 and 20 ng/mL) and concentrated rIL-25 at 10 ng/mL. A negative control of the culture medium (filtered supernatant of *L. lactis* pGroEL-Nuc) was used and equivalent protein amount corresponding to the concentration used with concentrated rIL-25 was added. 72 h after stimulation, cells supernatant were harvested for IL-5 or IL-13 quantification by ELISA.

Detection of Cytokines (IL-25, TSLP, IL-5, IL-13 and IL-12)

Different ELISA kits were used to quantify cytokines: IL-12 (mabTech), IL-13 (eBiosciences), IL-5 (mabTech), TSLP (eBiosciences) and IL-25 (eBiosciences and R&D systems).

Statistical Analysis

Results are expressed as mean values+/−SD of 3-6 samples. Student's t test was performed to determine statistical significance (*,  and * indicate $P<0.05$, $P<0.01$ and P<0.001, respectively) between condition of interest and the conditions a, b or c as indicated on figures.

Results

Growth Curves

1) NICE System—Normal Conditions

*L. lactis* pNis-cytokine

The plasmid pNis, also named pSEC, (Bermúdez-Humarán et. al. 2003 FEMS Microbiol, 224, 307-3013) is a derivative of the broad-host range plasmid pWV01 (Kok, van der Vossen et al. 1984, Appl Environ Microbiol, 48, 726-731) containing a nisin-inducible promoter and a signal peptide of Usp45 protein, the predominant *L. lactis*-secreted protein (de Ruyter, Kuipers et al. 1996, Appl Environ Microbiol, 62, 3662-3667). This plasmid contains Rep A and Rep C replication origins which allow to replicate in either Gram + or Gram −.

The pNis-cytokine plasmids were constructed and transformed in *L. lactis*. After verification by sequencing, the first step of strain characterization was to determine the bacterial growth in a classical laboratory rich culture medium: M17. Bacterial growth curves were performed into 96 wells plate in M17 supplemented with 1% glucose and 10 ng/mL chloramphenicol for strains containing plasmids (FIG. 1). Wild-type *L. lactis* NZ9000 strain without plasmid was used as a negative control. The slight delay in the bacterial growth of recombinant strains could be due to the presence of chloramphenicol antibiotic in the culture medium. No impairment in the growth of *L. lactis* strains harboring pNis plasmids encoding for IL-25, IL-25-His, TSLP or TSLP-His was observed.

*L. casei* pNis-cytokine

Figure 2:
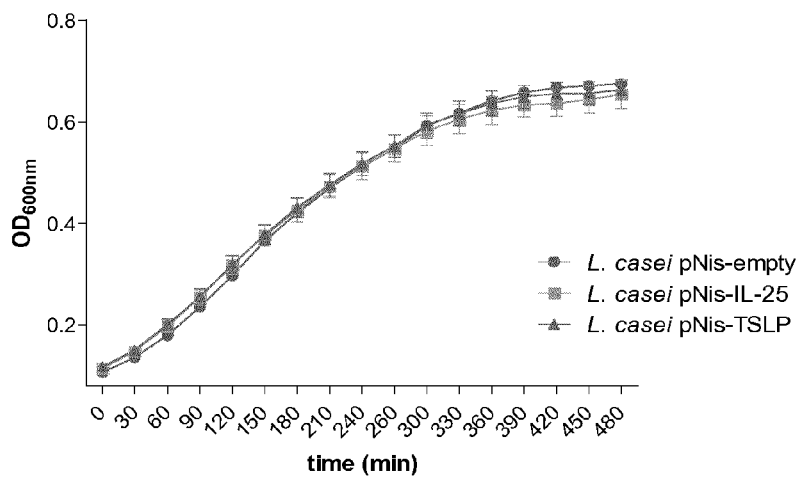
FIG. 2: Bacterial growth curves of *L. casei* pNis-empty, *L. casei* pNis-IL-25 and *L. casei* pNis-TSLP in MRS medium supplemented with 10 µg/mL chloramphenicol.

The pNis-Cytokine plasmids were constructed and transformed in *L. casei*. The bacterial growth of these strains was determined in MRS supplemented with 10 ng/mL chloramphenicol using a 96 wells plate (FIG. 2). *L. casei* pNis-empty was chosen to be the reference strain due to the presence of the pNis plasmid and so growth into a complex medium supplemented with chloramphenicol, as other strains. No impairment in bacterial growth of *L. casei* harboring pNis plasmids encoding for IL-25 or TSLP was observed.

2) NICE System—Stress Conditions

*L. lactis* pNis-cytokine

Figure 3:
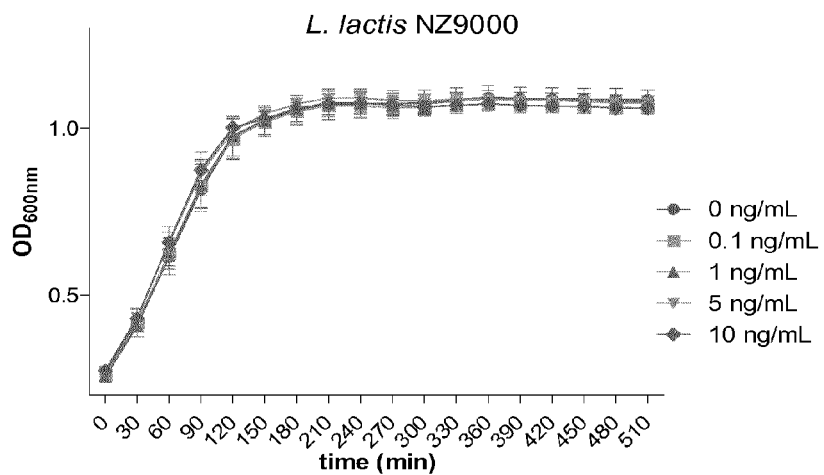
FIG. 3: Bacterial growth curves of *L. lactis* pNis-empty in M17 medium supplemented with 0.5% of glucose, 10 µg/mL chloramphenicol and 0, 0.1, 1, 5 or 10 ng/mL nisin.
Figure 4:
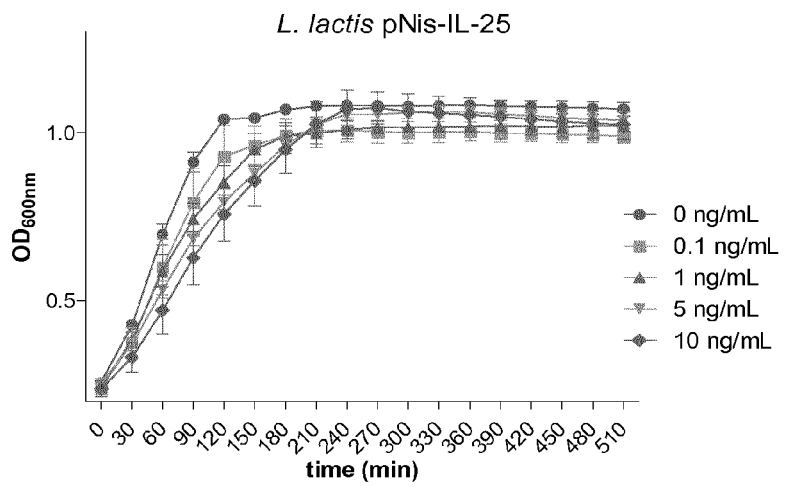
FIG. 4: Bacterial growth curves of *L. lactis* pNis-IL-25 in M17 medium supplemented with 0.5% of glucose, 10 µg/mL chloramphenicol and 0, 0.1, 1, 5 or 10 ng/mL nisin.
Figure 5:
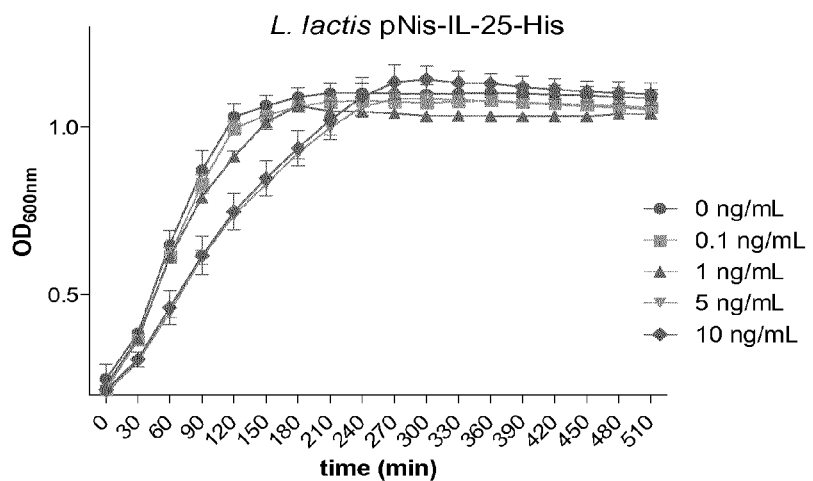
FIG. 5: Bacterial growth curves of *L. lactis* pNis-IL-25-His in M17 medium supplemented with 0.5% of glucose, 10 µg/mL chloramphenicol and 0, 0.1, 1, 5 or 10 ng/mL nisin.
Figure 6:
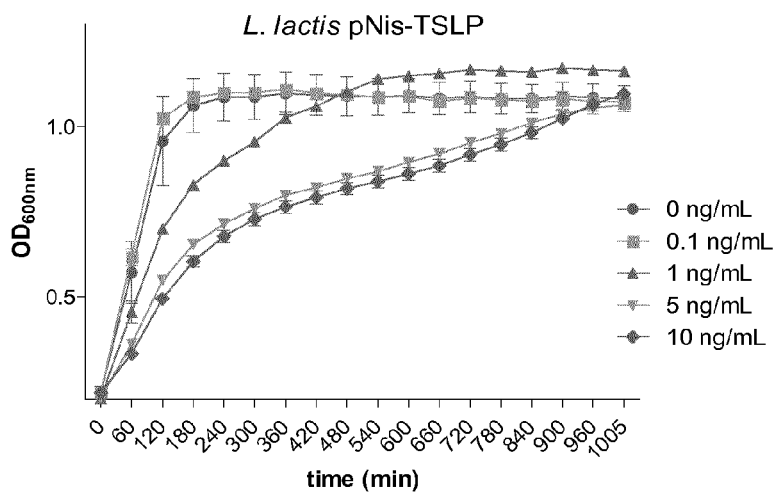
FIG. 6: Bacterial growth curves of *L. lactis* pNis-TSLP in M17 medium supplemented with 0.5% of glucose, 10 µg/mL chloramphenicol and 0, 0.1, 1, 5 or 10 ng/mL nisin.
Figure 7:
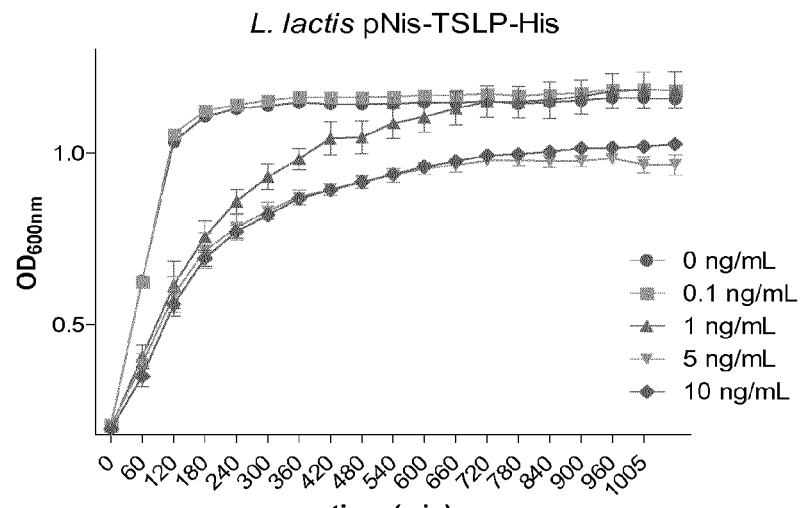
FIG. 7: Bacterial growth curves of *L. lactis* pNis-TSLP-His in M17 medium supplemented with 0.5% of glucose, 10 µg/mL chloramphenicol and 0, 0.1, 1, 5 or 10 ng/mL nisin.

Since gene expression in pNis plasmids is controlled by the nisin as inducer, the inventors then analyzed bacterial growth in presence of this bacteriocin. No impairment in the bacterial growth of the pNis-empty strains was observed in presence of nisin (at least at the tested concentrations) was observed (FIG. 3). Therefore, they concluded that nisin is not toxic for our recombinant strains. However, a short delay in the bacterial growth of *L. lactis* pNis-IL25 and pNis-IL25-His strains were observed with either 1 ng/mL or higher concentrations of nisin (FIG. 4 and FIG. 5). These growth impairments were much higher when nisin was added into culture of *L. lactis* pNis-TSLP and pNis-TSLP-His (FIG. 6 and FIG. 7). As observed, the presence of 0.1 ng/mL of nisin had no effect on the bacterial growth, reflecting bacterial growth without nisin. The higher growth delay was observed with 5 ng/mL of nisin. The growth profile of bacteria in presence of 10 ng/mL were very similar than that one observed with 5 ng/mL. Addition of 1 ng/mL nisin, allows to an intermediary growth phenotype. Addition of nisin in medium slowed down bacterial growth. This decrease may due to a toxicity of the produced recombinant cytokine, since this phenomenon has been frequently reported in other recombinant strains.

*L. casei* pNis-cytokine

Figure 8:
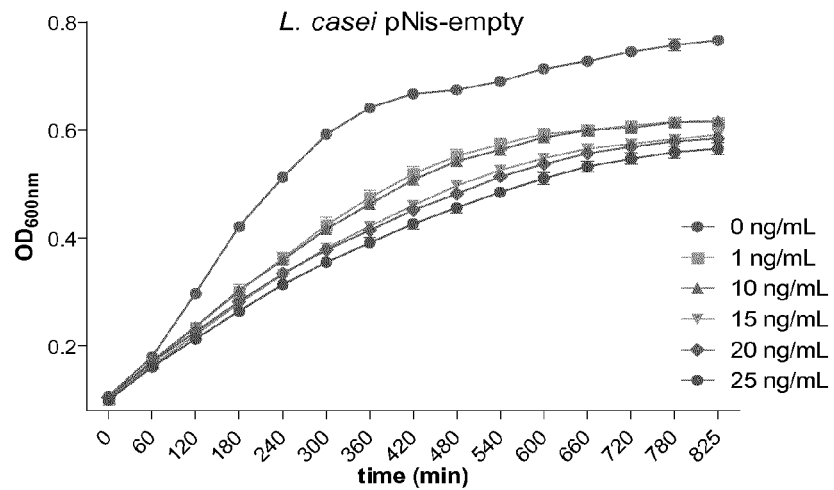
FIG. 8: Bacterial growth curves of *L. casei* pNis-empty in MRS medium supplemented with 10 µg/mL chloramphenicol and 0, 1, 10, 15, 20 or 25 ng/mL nisin.
Figure 9:
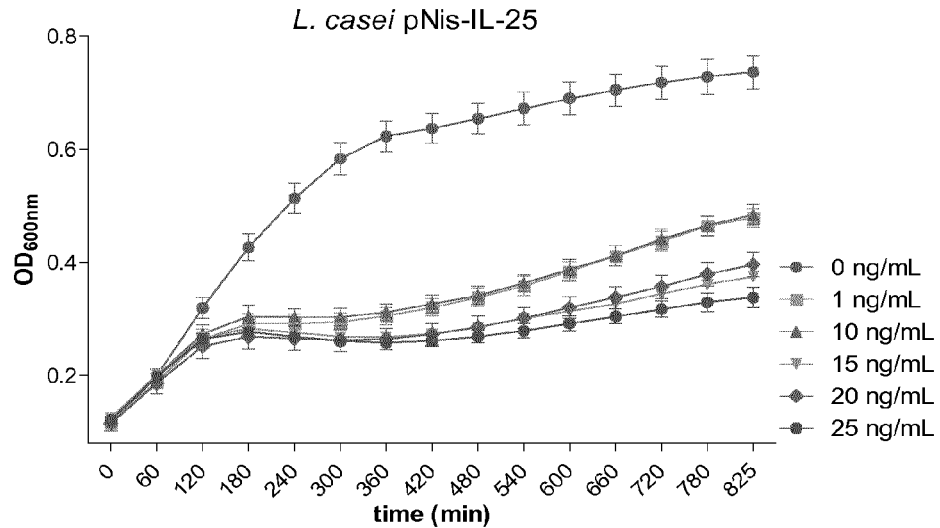
FIG. 9: Bacterial growth curves of *L. casei* pNis-IL-25 in MRS medium supplemented with 10 µg/mL chloramphenicol and 0, 1, 10, 15, 20 or 25 ng/mL nisin.
Figure 10:
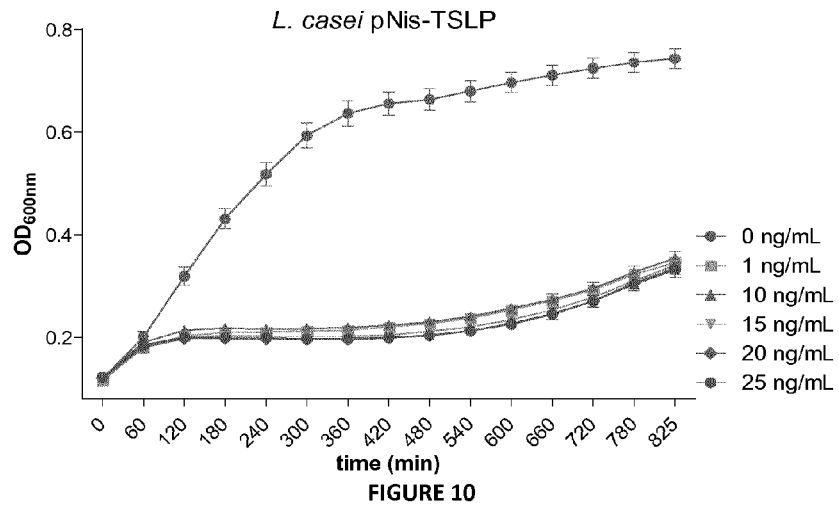
FIG. 10: Bacterial growth curves of *L. casei* pNis-IL-25 in MRS medium supplemented with 10 µg/mL chloramphenicol and 0, 1, 10, 15, 20 or 25 ng/mL nisin.

The inventors performed the same experiments with *L. casei* pNis-cytokine strains in the presence of nisin. A defect in their bacterial growth in presence of nisin at the tested concentrations was observed in pNis-empty strains (FIG. 8), suggesting that nisin is deleterious for *L. casei* growth. Furthermore, the delay of *L. lactis* pNis-IL25 and *L. lactis* pNis-TSLP strains was dramatically increased from 1 ng/mL nisin (FIG. 9 and FIG. 10).

Figure 11:
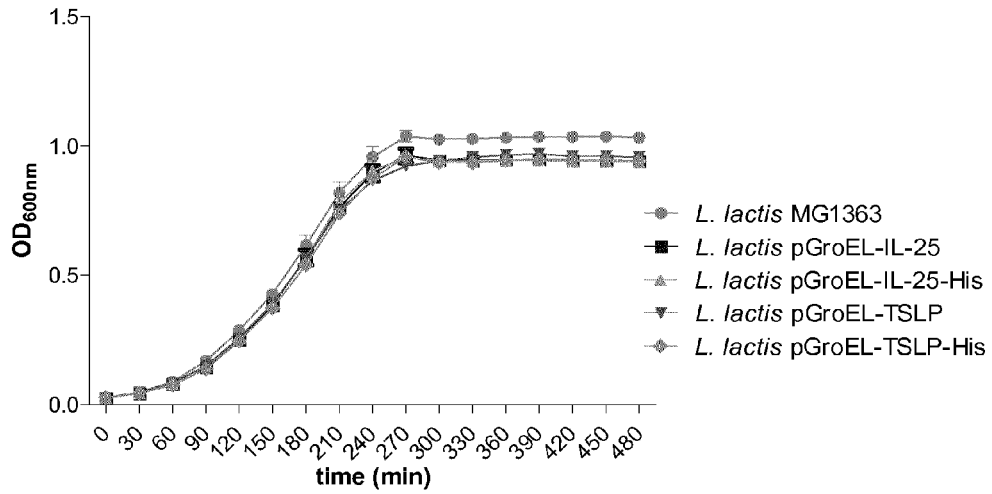
FIG. 11: Bacterial growth curves of *L. lactis* wild type (MG1363), *L. lactis* pGroEL-IL-25, pGroEL-IL25-His, pGroEL-TSLP and pGroEL-TSLP-His in M17 medium supplemented with 0.5% glucose and 10 µg/mL chloramphenicol.

3) SICE System—Normal Conditions pGroEL plasmid (WO2013/175358) is a derivative of the broad-host range plasmid pWV01 (Kok, van der Vossen et al. 1984, supra) containing a promoter from GroEL protein, a *L. lactis* MG1363 protein induced in stress conditions as acidic pH, high temperature and bile salts and most important, in the gastro-intestinal tract of mice (Kilstrup, Jacobsen et al. 1997, Appl Environ Microbiol, 63, 1826-1837; Roy, Meyrand et al. 2008, Proteomics 8, 1661-1676). It also contains a peptide signal of Exp4 protein, a well-secreted protein in *L. lactis* (Poquet, Ehrlich et al. 1998, J Bacteriol, 180, 1904-1912) and Rep A and Rep C replication origins which allow to replicate in either Gram + or Gram −. This plasmid is only functional in *L. lactis* due to the specificity of GroEL promoter.

pGroEL-cytokine plasmids were constructed and established in *L. lactis*. After validation by sequencing, the inventors proceeded, as for pNis-cytokine plasmids, to determine bacterial growth. Bacterial growth curves were performed into 96 wells plate in M17 supplemented with 1% glucose and 10 ng/mL chloramphenicol for strains containing plasmids (FIG. 11). Wild-type *L. lactis* MG1363 strain without plasmid was used as control. The slight delay in the bacterial growth of recombinant strains could be due to the presence of chloramphenicol antibiotic in the culture medium. No impairment in the growth of *L. lactis* strains harboring pGroEL plasmids encoding for IL-25, IL-25-His, TSLP or TSLP-His was observed.

4) SICE System—Stress Conditions

Since gene expression in pGroEL-cytokine plasmid is controlled by stress conditions, the inventors next analyzed bacterial growth in presence of stress. These stress assays were performed to analyze both cytokine production and secretion and bacterial growth.

Salt Stress

Figure 12:
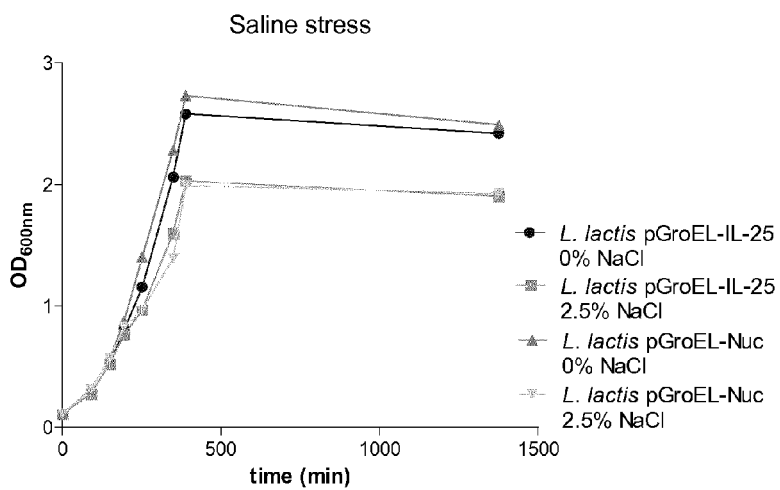
FIG. 12: Bacterial growth curves of *L. lactis* pGroEL-Nuc and *L. lactis* pGroEL-IL-25 in M17 medium supplemented with 0.5% glucose, 10 µg/mL chloramphenicol and with or without 2.5% NaCl.
Figure 13:
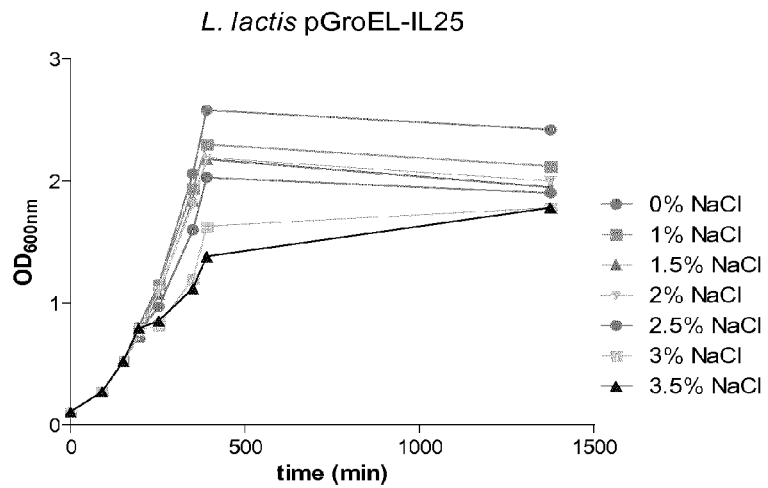
FIG. 13: Bacterial growth curves of *L. lactis* pGroEL-IL-25 in M17 medium supplemented with 0.5% glucose, 10 µg/mL chloramphenicol and 0, 1, 1.5, 2, 2.5, 3 or 3.5% NaCl.
Figure 14:
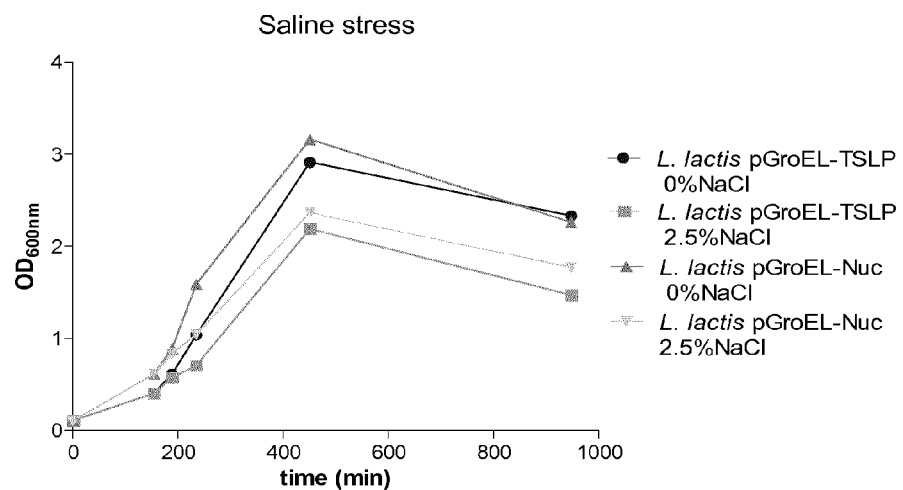
FIG. 14: Bacterial growth curves of *L. lactis* pGroEL-Nuc and *L. lactis* pGroEL-TSLP in M17 medium supplemented with 0.5% glucose, 10 µg/mL chloramphenicol and with or without 2.5% NaCl.
Figure 15:
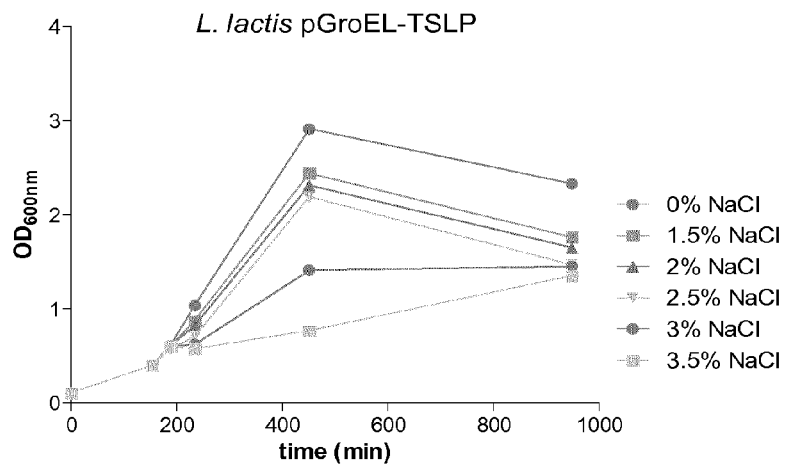
FIG. 15: Bacterial growth curves of *L. lactis* pGroEL-TSLP in M17 medium supplemented with 0.5% glucose, 10 µg/mL chloramphenicol and 0, 1, 1.5, 2, 2.5, 3 or 3.5% NaCl.

*L. lactis* pGroEL-Nuc, *L. lactis* pGroEL-IL-25 and *L. lactis* pGroEL-TSLP have similar growth curves and show an identical impairment in their bacterial growth in presence of 2.5% NaCl (FIG. 12 and FIG. 14). This growth delay is observed from 1% NaCl and the more the NaCl concentration is increased, the more the bacterial growth is impaired (FIG. 13 and FIG. 15).

Heat-shock

Figure 16:
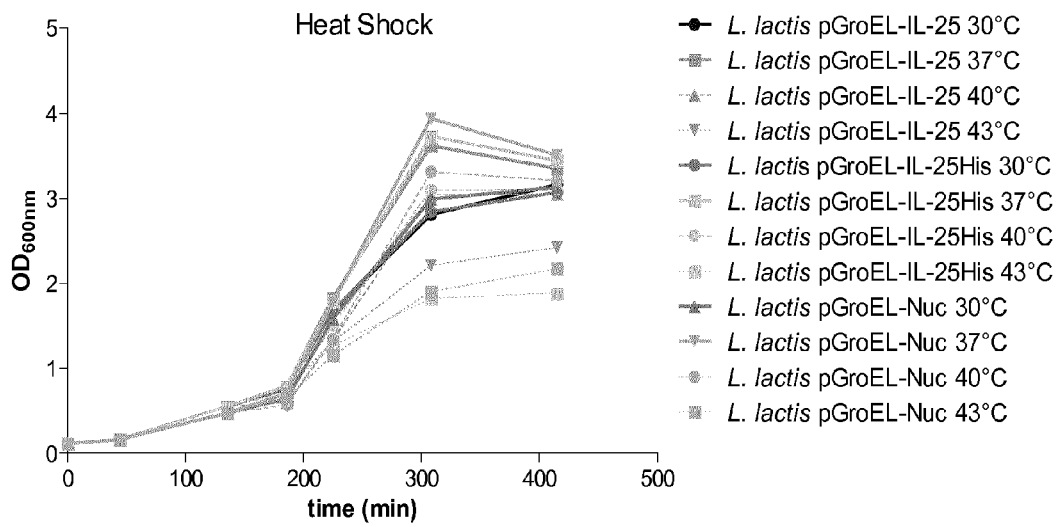
FIG. 16: Bacterial growth curves of *L. lactis* pGroEL-Nuc, *L. lactis* pGroEL-IL-25 and *L. lactis* pGroEL-IL-25-His in M17 medium supplemented with 0.5% glucose, 10 µg/mL chloramphenicol and at 30° C., 37° C. or 40° C.
Figure 17:
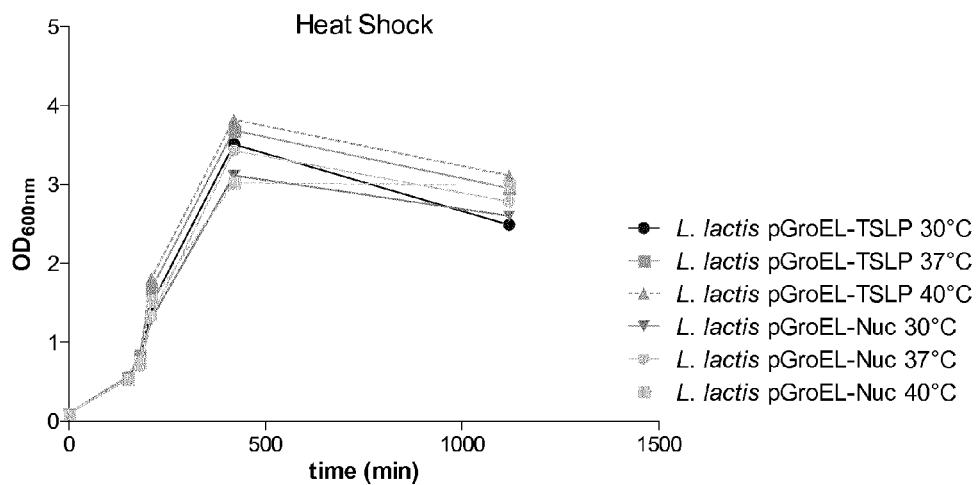
FIG. 17: Bacterial growth curves of *L. lactis* pGroEL-Nuc and *L. lactis* pGroEL-TSLP in M17 medium supplemented with 0.5% glucose, 10 µg/mL chloramphenicol and at 30° C., 37° C., 40° C. or 43° C.

*L. lactis* pGroEL-IL-25, *L. lactis* pGroEL-IL-25-His, *L. lactis* pGroEL-TSLP and *L. lactis* pGroEL-Nuc strains have similar growth curves for the different temperature conditions (FIG. 16 and FIG. 17). At 30° C., 37° C. and 40° C., the exponential phase of these strains are identical but at 37° C., strains reach a higher $OD_{600\ nm}$ value for the stationary phase. At 43° C., the *L. lactis* pGroEL-IL-25, *L. lactis* pGroEL-IL-25-His and *L. lactis* pGroEL-Nuc show the same growth impairment (FIG. 16).

Acidic pH Stress

Figure 18:
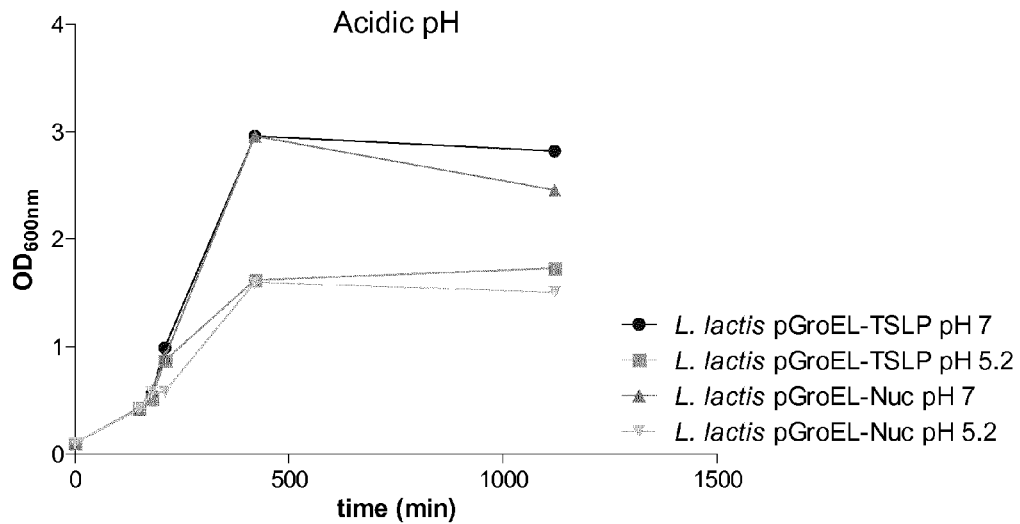
FIG. 18: Bacterial growth curves of *L. lactis* pGroEL-Nuc and *L. lactis* pGroEL-TSLP in M17 medium supplemented with 0.5% glucose, 10 µg/mL chloramphenicol and at pH7 or pH5.2.

*L. lactis* pGroEL-Nuc and *L. lactis* pGroEL-TSLP have similar growth curves and show an identical impairment in their bacterial growth in acidic pH (FIG. 18).

Cytokine Secretion Using NICE System

The inventors performed several tests using different nisin concentrations to determine cytokine production and secretion by recombinant LAB. Samples (supernatant fraction: S, and bacterial cell lysates: C) were collected 30 min, 5 h and 24 h before nisin induction and cytokine concentration were measured by ELISA in S and C samples.

No significant cytokine production of either IL-25 or TSLP was detected in C samples. This failure in the detection by ELISA can be due to a different conformational cytokine form caused by the presence of the signal peptide in the non-secreted protein form in the bacterial cell (ie. C sample). The inventors thus focus their experiments in S samples. However, some Western Blot experiments were also performed for IL-25-His production by recombinant *L. lactis*.

Figure 19:
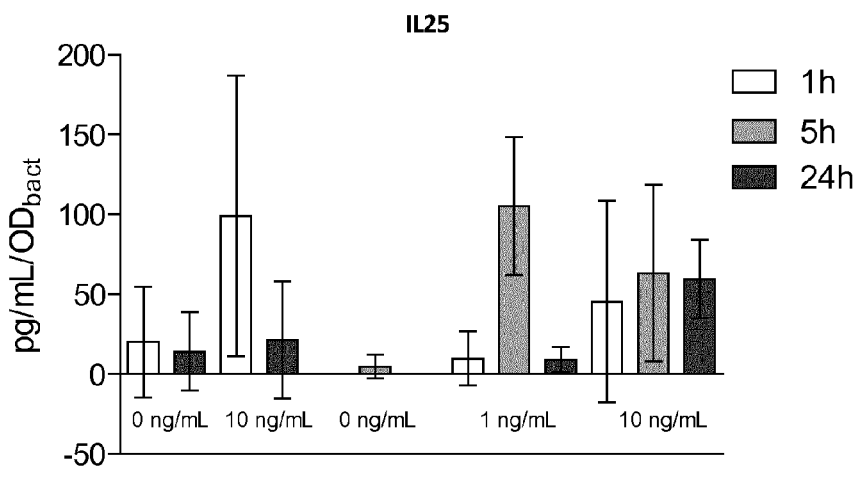
FIG. 19: Detection by ELISA of IL-25 in supernatant fractions from nisin-induced (0, 1 or 10 ng/mL) cultures of *L. lactis* pNis-IL-25 and *L. lactis* pNis-Nuc strains.

Secretion of IL-25 by *L. lactis*: As shown in the FIG. 19, the levels of IL-25 were not significantly different in S samples from induced-cultures of *L. lactis* pNis-IL-25 and *L. lactis* pNis-Nuc strains at the different time points tested and with the different nisin concentrations. The inventors can thus conclude that *L. lactis* pNis-IL-25 does not secrete IL-25 under these conditions.

Figure 20:
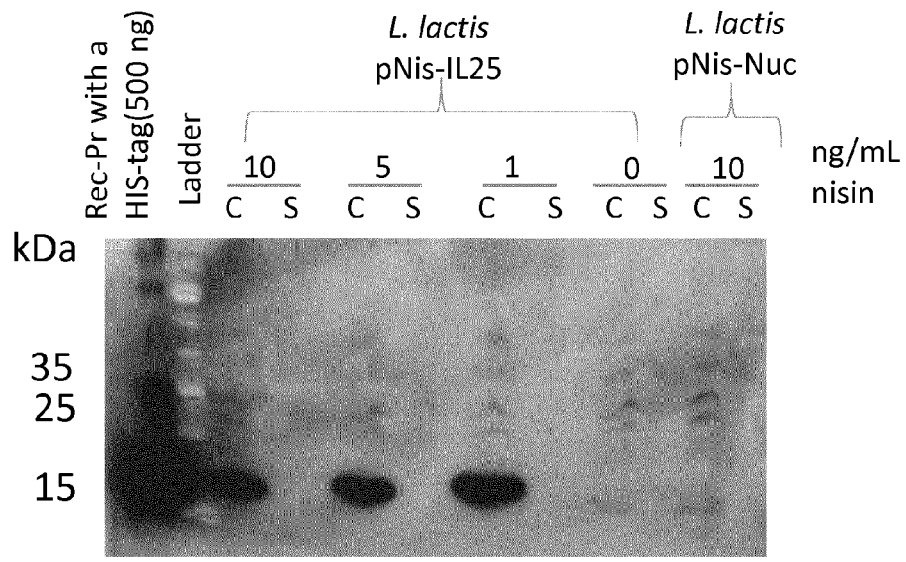
FIG. 20: Detection by Western Blot of IL-25-His either in bacterial cell lysates (C) or supernatant fractions (S) samples from nisin-induced (0, 1 or 10 ng/mL) cultures of *L. lactis* pNis-IL-25-His and *L. lactis* pNis-Nuc strains.

Production of IL-25-His by *L. lactis*: The inventors then analyzed IL-25-His production and secretion by *L. lactis* pNis-IL-25-His by Western Blot. As shown in the FIG. 20, IL-25-His is detected in C samples from induced-cultures of *L. lactis* pNis-IL-25-His strain but not in S fractions. Similar amounts of IL-25-His were detected in C fractions after induction with the 3 different doses of nisin (ie. 1, 5 and 10 ng/mL). In the absence of nisin, no IL-25-His signal was detected confirming that this system is tightly regulated. Altogether, ELISA and Western blot experiments confirm that there is no IL-25 secretion by recombinant *L. lactis*. This phenomenon has been previously observed for other heterologous proteins produced in *L. lactis* and could be due to a weak processing and secretion of the precursor form of IL-25-His recombinant cytokine.

Figure 21:
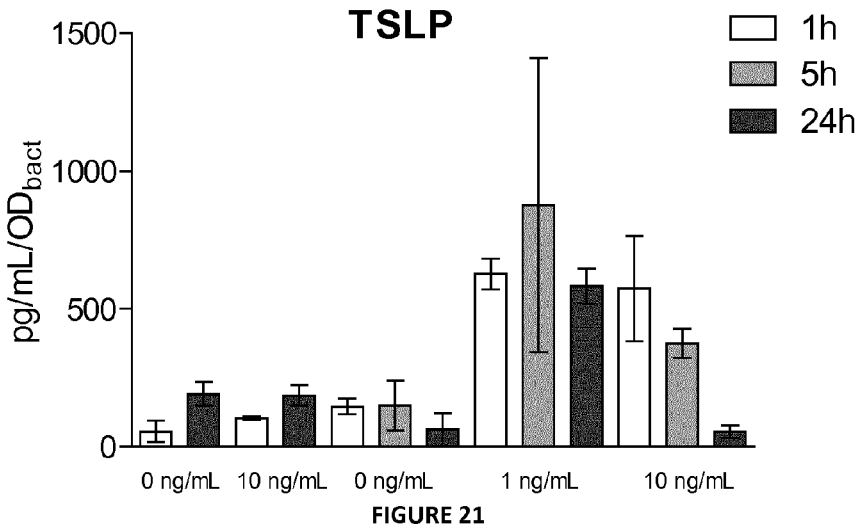
FIG. 21: Detection by ELISA of TSLP in supernatant fractions from nisin-induced (0, 1 or 10 ng/mL) cultures of *L. lactis* pNis-TSLP and *L. lactis* pNis-Nuc strains.

Secretion of TSLP by *L. lactis*: No significant TSLP production was detected in the absence of nisin in S samples from *L. lactis* pNis-TSLP cultures since the observed signal is at the same level of S samples from either non-induced or nisin-induced (10 ng/mL) of our negative control strain: *L. lactis* pNis-Nuc (FIG. 21). Strikingly, S samples from induced-*L. lactis* pNis-TSLP cultures reveal a clear production and secretion of TSLP (FIG. 21). Incubation for 1 h with nisin show that there is no significant difference in TSLP secretion between the two doses of nisin tested (1 and 10 ng/mL). However, time-course experiments indicated that, at a concentration of 1 ng/ml of nisin, TSLP accumulated in the culture medium for about 5 h, reaching a maximal concentration of about 1000 pg/ml.

Figure 22:
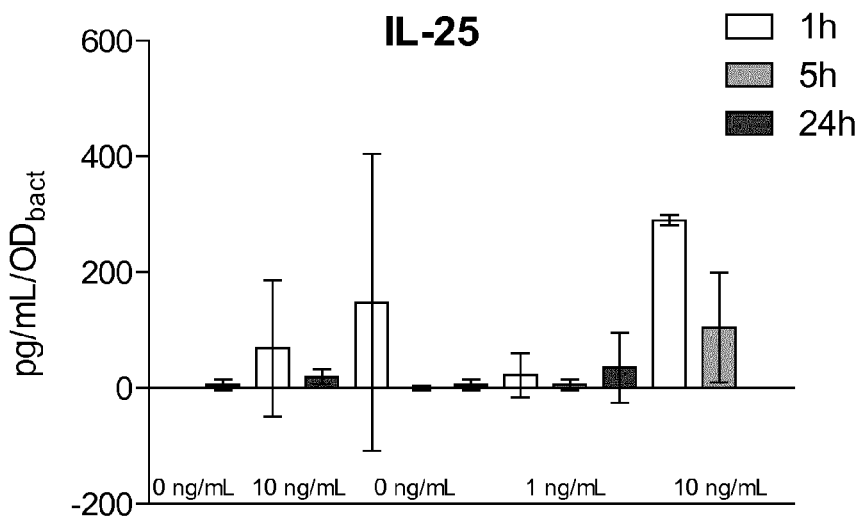
FIG. 22: Detection by ELISA of IL-25 in supernatant fractions from nisin-induced (0, 1 or 10 ng/mL) cultures of *L. casei* pNis-IL-25 and *L. casei* pNis-Nuc strains.
Figure 23:
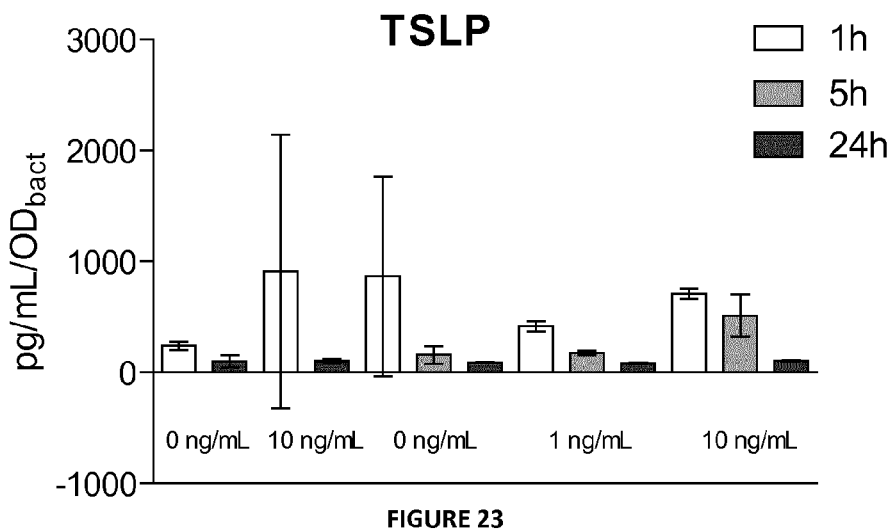
FIG. 23: Detection by ELISA of TSLP in supernatant fractions from nisin-induced (0, 1 or 10 ng/mL) cultures of *L. casei* pNis-TSLP and *L. casei* pNis-Nuc strains.

Secretion of cytokine by *L. casei*: The levels of detected IL-25 (FIG. 22) or TSLP (FIG. 23) were not significantly different in S samples from nisin-induced *L. casei* pNis-IL-25, *L. casei* pNis-TSLP and *L. lactis* pNis-Nuc cultures at the different time points tested and in presence of the different nisin concentrations. Recombinant *L. casei* does not secrete IL-25 and TSLP cytokines under these conditions.

Cytokine Secretion Using SICE System

The inventors performed several tests using different stress (eg. salts stress, heat shock and acidic pH) to determine cytokine production and secretion by recombinant LAB using the SICE system. S and C samples were collected 30 min, 4 h, 5 h and 24 h before stress-induction and cytokine concentration were measured by ELISA in S and C samples.

As for the NICE system, no significant cytokine production of either IL-25 or TSLP was detected in C samples and the inventors only present experiments performed in S samples analyzed by ELISA.

Figure 24:
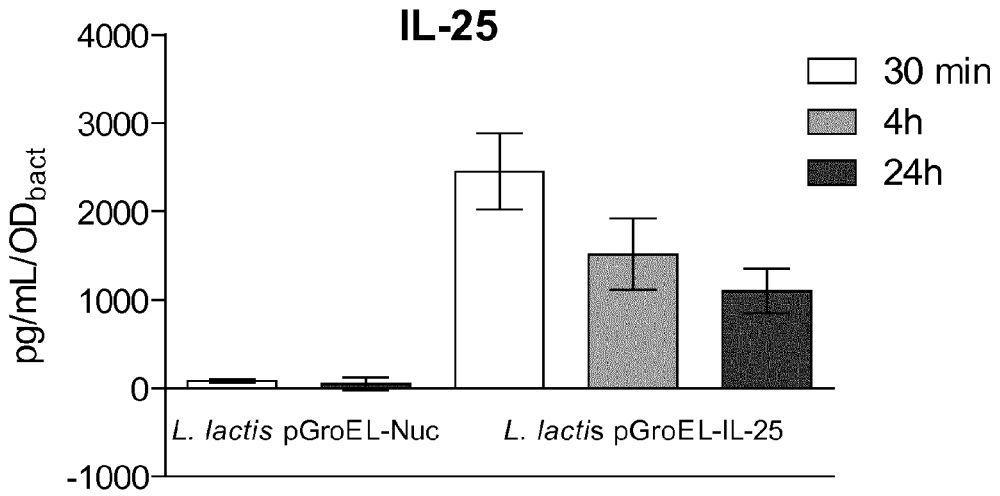
FIG. 24: Detection by ELISA of IL-25 in supernatant fractions from *L. lactis* pNis-IL-25 and *L. lactis* pNis-Nuc cultures.
Figure 25:
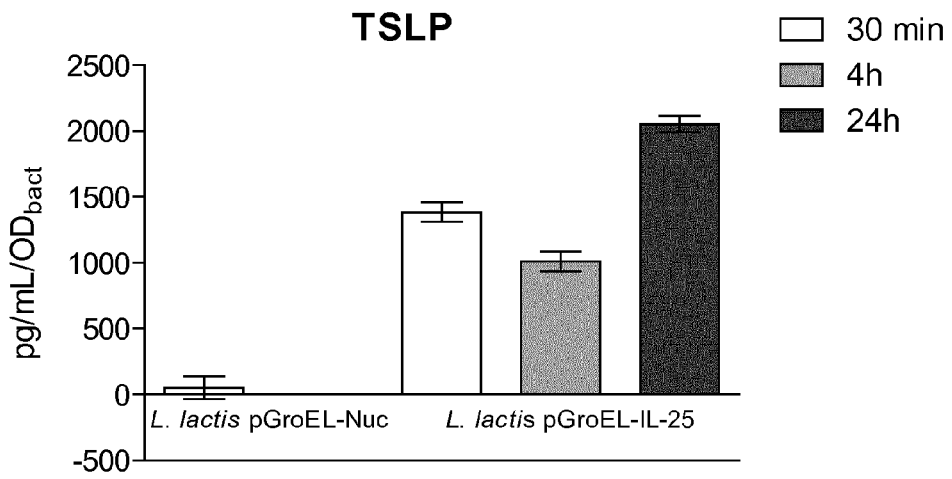
FIG. 25: Detection by ELISA of TSLP in supernatant fractions from *L. lactis* pNis-TSLP and *L. lactis* pNis-Nuc cultures.

Negative control: *L. lactis* pGroEL-Nuc: A weak signal was observed in the S fraction of *L. lactis* pNis-Nuc strain when compared to S samples from either *L. lactis* pNis-IL-25 (FIG. 24) or *L. lactis* pNis-TSLP (FIG. 24) strains, demonstrating that there is no background due to lactococcal proteins.

Figure 26:
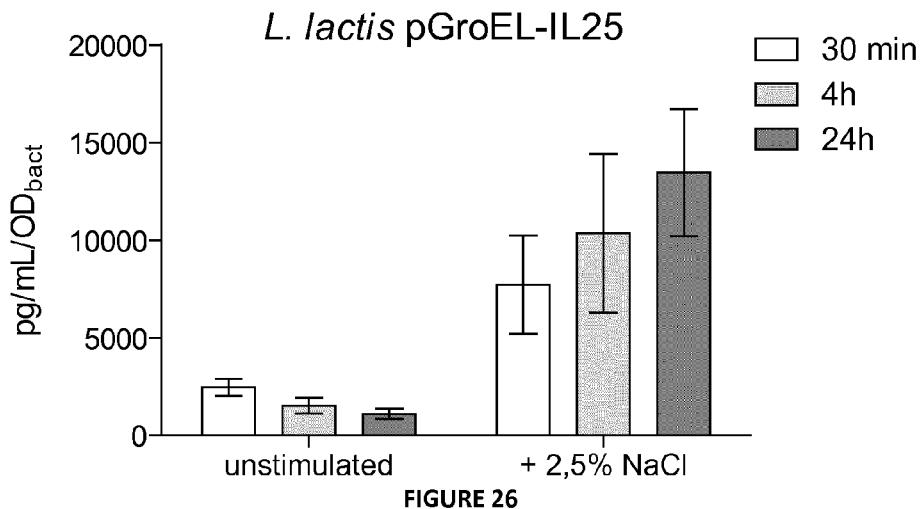
FIG. 26: Detection by ELISA (eBioscience) of IL-25 in supernatant fractions from NaCl-stress (2.5%) induced cultures of *L. lactis* pNis-IL-25.
Figure 27:
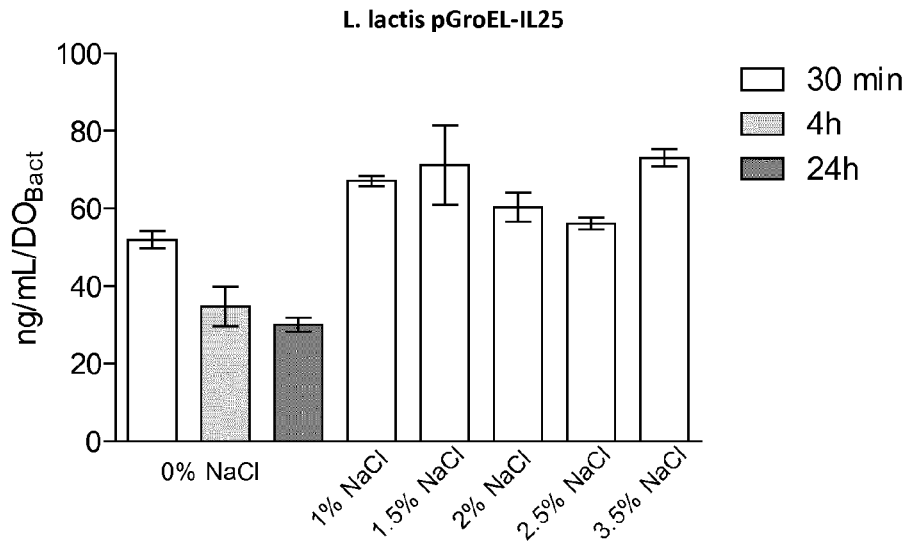
FIG. 27: Detection by ELISA of IL-25 in supernatant fractions from NaCl-induced 0.1, 1.5, 2, 2.5, 3 or 3.5%) culture of *L. lactis* pGroEL-IL-25 strain.
Figure 28:
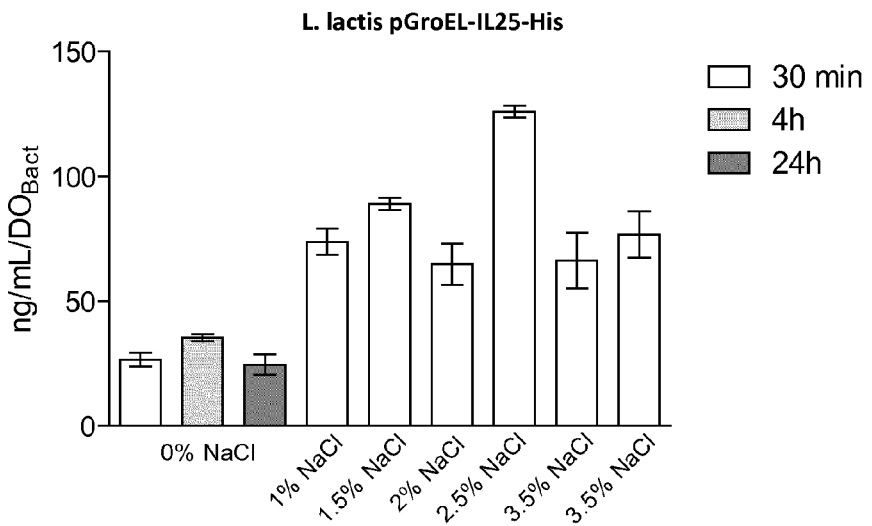
FIG. 28: Detection by ELISA of IL-25 in supernatant fractions of *L. lactis* pGroEL-IL-25 and after NaCl induction (0, 1, 1.5, 2, 2.5, 3 or 3.5%).

Salt stress—Secretion of IL-25 by *L. lactis*: *L. lactis* pGroEL-IL-25 secretes cytokine, showing that the promoter is functional (FIG. 26). Furthermore, the levels of detected IL-25 are significantly enhanced 3 times at 30 min, 7 times at 4 h and 12 times at 24 h in presence of 2.5% NaCl. This stress led to a strong increase of IL-25 by *L. lactis* pGroEL-IL-25. However, the inventors tested another ELISA kit from R&D Systems after several problems with this one from eBioscience. They obtained a 20-fold (or more) difference in the concentration measured on same samples by ELISA from R&D System or from eBioscience. They used R&D System Kit for the following results. The levels of detected IL-25 have the same profile than the previous results: a decrease of secretion/bacteria in the time course but with 20-30 times increased concentration values (FIG. 27 and FIG. 26). At 30 min, the inventors observed a significant enhancement of IL-25 secretion in presence of NaCl except at 2.5%. At 4 h, 24 h and 3% at 30 min, the sample dilution was not sufficient. The obtained values were above the standard and so underestimated. However and logically, these values are higher than presented on the graph, demonstrating an increase of IL-25 secretion by *L. lactis* pGroEL-IL-25 after a saline stress. One more time, the inventors did not dilute enough the samples (FIG. 28). However, the salt stress led to a strong increase (2/4 times) in IL-25-His secretion by *L. lactis* pGroEL-IL-25-His.

Figure 29:
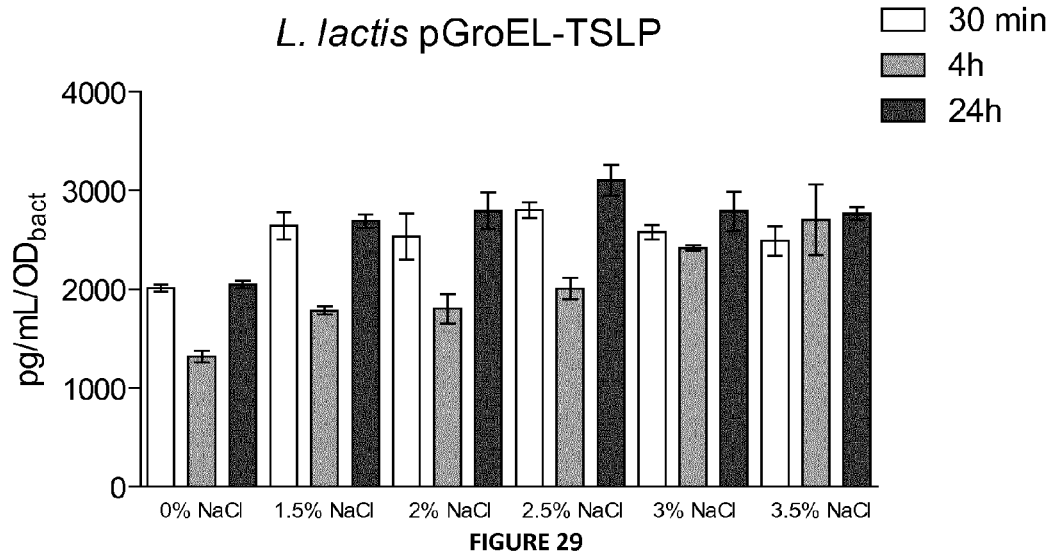
FIG. 29: Detection by ELISA of TSLP in supernatant fractions from NaCl-induced (0, 1, 1.5, 2, 2.5, 3 or 3.5%) cultures of *L. lactis* pGroEL-TSLP strain.

Salt stress—Secretion of TSLP by *L. lactis*: *L. lactis* pGroEL-TSLP was able to secret TSLP, demonstrating an opening of its promoter (FIG. 29). Levels of TSLP detected by ELISA are weakly increased (1.5 times) in presence of NaCl compare to the secretion by unstimulated *L. lactis* pGroEL-TSLP.

Figure 30:
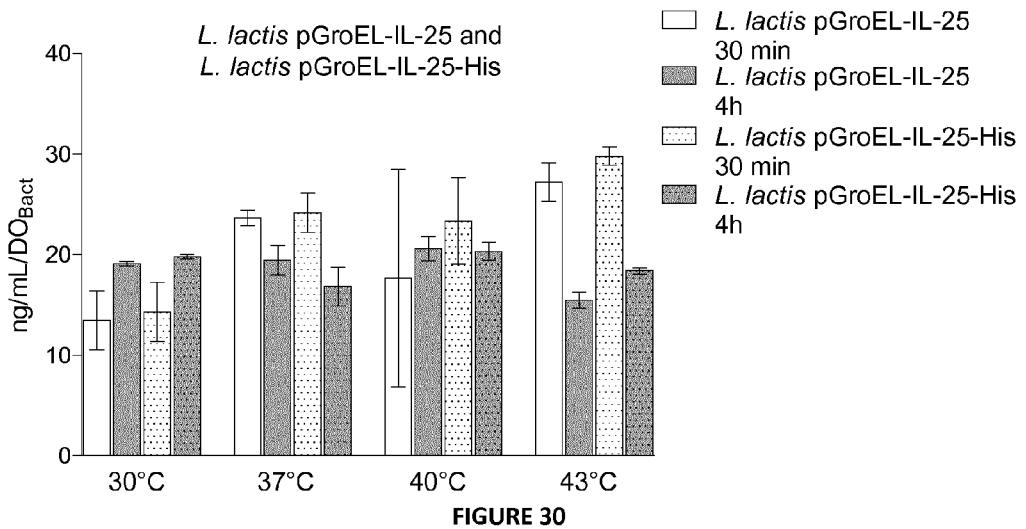
FIG. 30: Detection by ELISA of IL-25 in supernatant fractions from heat-shock-induced (30° C., 37° C., 40° C. or 43° C.) *L. lactis* pGroEL-IL-25 and *L. lactis* pGroEL-IL-25-His cultures.

Heat-shock—Secretion of IL-25 and IL-25-His by *L. lactis*: The inventors then tested the secretion induction by heat-shock. First of all, they detected equal amounts of IL-25 and IL-25-His at 30° C. and at 30 min and 4h, showing a similar secretion between IL-25 and IL-25-His by *L. lactis* (FIG. 30). They also observed an increase of secretion at 37° C. and 43° C., 30 min after heat shock. However, this increase is not observed 4h after heat shock.

Figure 31:
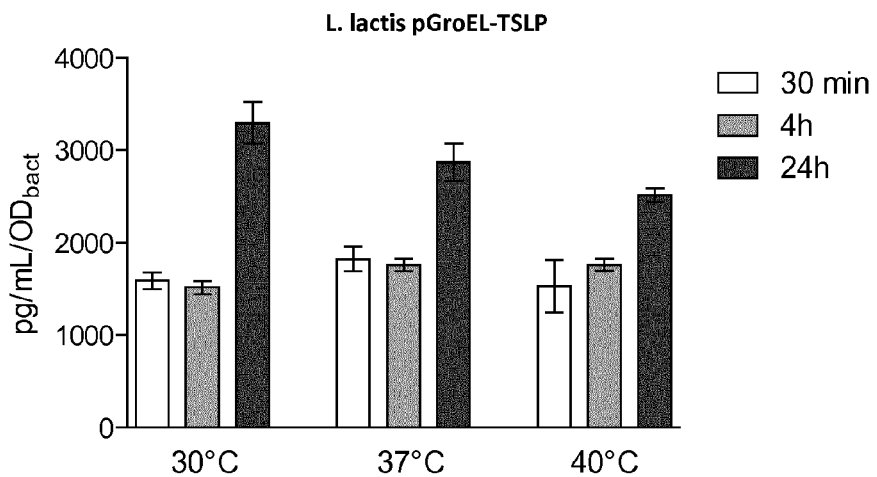
FIG. 31: Detection by ELISA of TSLP in supernatant fractions from heat-shock (30° C., 37° C. or 40° C.) *L. lactis* pGroEL-TSLP cultures.
Figure 32:
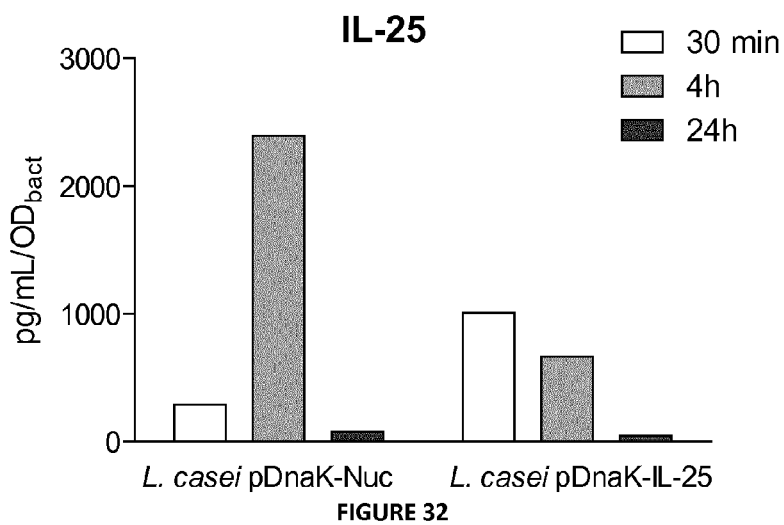
FIG. 32: Detection by ELISA of TSLP in supernatant fractions from *L. casei* pDnaK-IL-25 and *L. casei* pDnaK-Nuc cultures.

Heat-shock—Secretion of TSLP by *L. lactis*: The inventors thus tested the TSLP secretion after heat shock. They showed a slightly increased of this secretion at 37° C. and 40° C., 30 min and 4 h after heat shock by *L. lactis* (FIG. 31).

Heat-shock—Secretion of IL-25 by *L. casei*. The plasmid pDnaK is a derivative of the broad host range plasmid pWV01 (Kok, van der Vossen et al. 1984, supra) containing a promoter from DnaK, a *L. casei* BL23 protein induced in stress conditions as acidic pH and bile salts. It contains also a peptide signal of P40 protein, a secreted protein in *L. casei* and Rep A and Rep C replication origins which allow to replicate in either Gram +or Gram −. This plasmid is only functional in *L. casei* due to the specificity of DnaK promoter. The inventors observed a strong detection of IL-25 in supernatant of *L. casei* pDnak-Nuc, the negative control. They did not show an IL-25 secretion due to the high background of the experiment, suggesting a problem in the production or the secretion of this cytokine in the SICE system in *L. casei*. Then, the inventors demonstrated that cytokine production and secretion is increased in these strains after either a salt (1% NaCl) or heat-shock (37 and 42° C.) stress. Strikingly, they showed a biological activity of cytokines produced and secreted by recombinant *L. lactis*.

Cytokine Activity Test

The next and most important step was to validate the recombinant strains by verification of the biological activity of the secreted cytokines by *L. lactis*.

Figure 33:
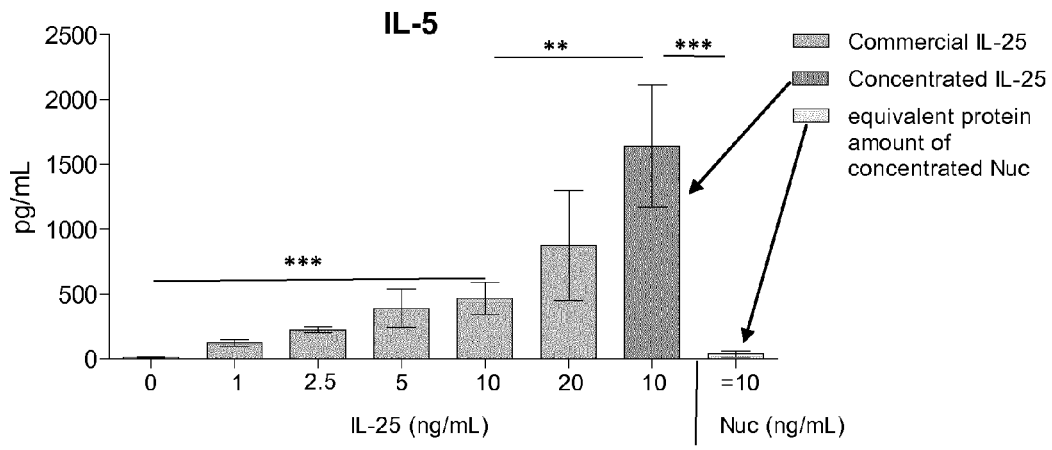
FIG. 33: Detection by ELISA of IL-5 in splenocytes supernatants stimulated with commercial IL-25 (0, 1, 2.5, 5, 10 or 20 ng/mL), with IL-25 from concentrated supernatant of *L. lactis* pGroEL-IL-25 (10 ng/mL) or with equivalent amount of protein from concentrated supernatant of *L. lactis* pGroEL-Nuc (negative control).
Figure 34:
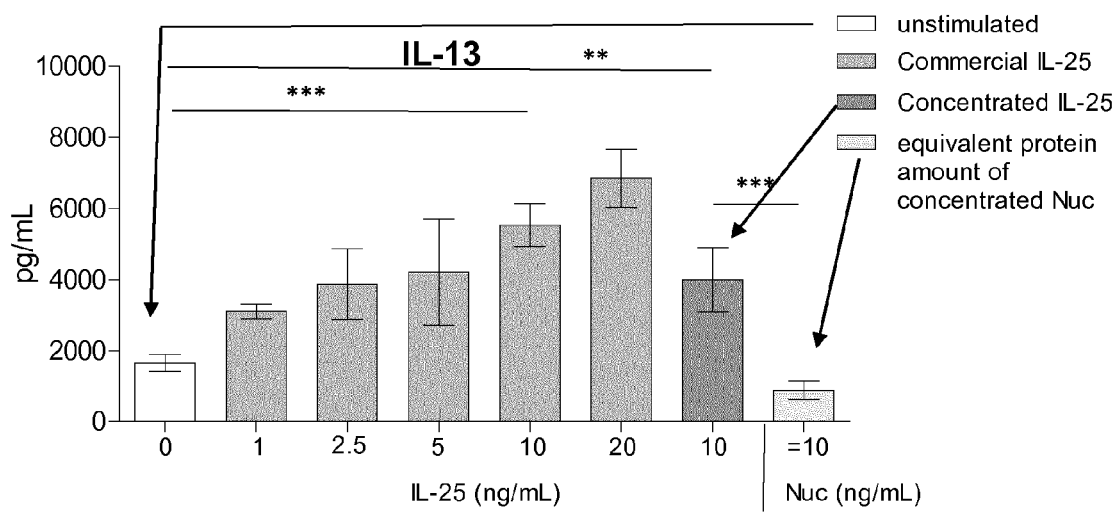
FIG. 34: Detection by ELISA of IL-13 in splenocytes supernatants stimulated with commercial IL-25 (0, 1, 2.5, 5, 10 or 20 ng/mL), with IL-25 from concentrated supernatant of *L. lactis* pGroEL-IL-25 (10 ng/mL) or with equivalent amount of protein from concentrated supernatant of *L. lactis* pGroEL-Nuc (negative control).

IL-25 activity test: Rickel et al has shown an IL-5 and IL-13 secretion by splenocytes when these cells were stimulated by IL-25 (Rickel, Siegel et al. 2008, J Immunol, 181, 4299-4310). Based on this paper, the inventors stimulated splenocytes with either commercial IL-25 or with the recombinant and concentrated IL-25. Seventy-two hours after stimulation, they recovered cell supernatants, and they measured IL-5 and IL-13 concentration in these samples. As shown in FIGS. 33 and 34 and as expected, no significant secretion of both IL-5 and IL-13 was observed in stimulated-cells with concentrated supernatant of *L. lactis* pGroEL-Nuc (negative control) compared to the unstimulated condition. However, the inventors detected an increase in IL-5 and IL-13 secretion after stimulation with commercial IL-25 and this increase is dose-dependent (FIGS. 33 and 34). They also demonstrated an increase in IL-5 and IL-13 secretion after stimulation with the present recombinant IL-25, demonstrating a biological activity of IL-25 produced by recombinant *L. lactis*.

Figure 35:
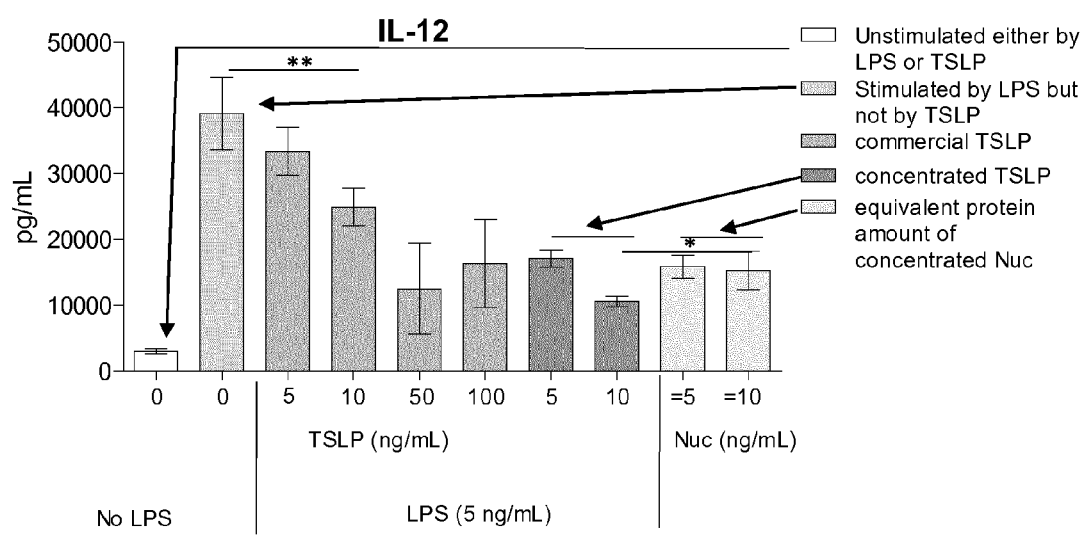
FIG. 35: Detection by ELISA of IL-12 in LPS-stimulated-BMDCs supernatants stimulated with commercial TSLP (0, 5, 10, 50 or 100 ng/mL), with IL-25 from concentrated supernatant of *L. lactis* pGroEL-IL-25 (5 or 10 ng/mL) or with equivalent amount of protein from concentrated supernatant of *L. lactis* pGroEL-Nuc (negative control).

TSLP activity test: Taylor et al has shown a decrease of IL-12 secretion by LPS-stimulated-BMDCs after TSLP-stimulation (Taylor, Zaph et al. 2009, J Exp Med, 206, 655-667). Based on these results, the inventors performed a LPS-stimulated-BMDCs assay with commercial TSLP and with the present recombinant and concentrated TSLP produced by *L. lactis*. Twenty-four h after the stimulation, they recovered cell supernatants, and we measured IL-12 concentration in the samples. The inventors observed a significant secretion of IL-12 when they stimulated cells with concentrated supernatant of *L. lactis* pGroEL-Nuc (negative control) compare to the unstimulated condition (FIG. 35). They detected a decrease of IL-12 secretion after stimulation with commercial TSLP and this decrease is dose-dependent. They showed a significant decrease of IL-12 secretion with our recombinant TSLP, demonstrating a biological activity of TSLP. They thus validated the *L. lactis* pGroEL-TSLP strain.

These cytokines, secreted by *L. lactis*, are biologically active. IL-25 secreted by *L. lactis* is able to stimulate splenocytes. Indeed, these cells secrete IL-5 and IL-13 after 72 h stimulation by either our recombinant IL-25 or "commercial" IL-25. Moreover, TSLP secreted by *L. lactis* induced an IL-12 secretion decrease by LPS-stimulated-BMDCs, showing that our recombinant TSLP is biological active as it can interact with BMDCs. These experiments allowed the inventors to validate these recombinant strains.

These promising results represent a step toward the evaluation of the immuno-modulatory and prophylactic effects of recombinant *L. lactis* strains expressing IL-25 and TSLP in vivo.

Evaluation of the Immunomodulatory and Prophylactic Properties of Recombinant *L. lactis* Expressing muIL-25 and muTSLP in Two Chemically-Induced Mouse Models of Colitis Different chemically-induced mouse models of colitis (eg. TNBS, DNBS, DSS, IL-10 KO, etc.) are currently used in the inventors' laboratory in order to determine the beneficial effects of either candidate bacteria or molecules. They decided to use two mouse models of colitis chemically-induced by dextran sulfate sodium (DSS) or dinitrobenzene sulfonic acid (DNBS).

Indeed, DSS induces colitis characterized by bloody diarrhea, ulcerations and granulocytes infiltration. This molecule is known to directly affect the basal crypts of gut epithelial cells and therefore affects integrity of the mucosal barrier. DSS colitis model is particularly useful to study and characterize the contribution of innate immune mechanisms of colitis. In contrast, DNBS-induced colitis model is used to decipher T helper cell-dependent mucosal immune responses. DNBS is prepared in ethanol (that perturb the mucosal barrier), whereas DNBS will haptenize colonic autologous or microbiota proteins rendering them immunogenic to the host immune system, resulting in an inflammation.

Both models are driven by different pathways and will thus help us to decipher the mechanisms of action of our recombinant strains.

Example 2

Evaluation of the Immuno-Modulatory and Prophylactic Effects of Recombinant *L. lactis* Strains Expressing TSLP In Vivo Summary To understand the role of TSLP in inflammatory processes, the inventors constructed *Lactococcus lactis* strain producing TSLP (LL-TSLP) and investigated the effect of its administration on a colitis model in mice. Treatment with LL-TSLP, increases the amount of TGF-β secreted by T cells in healthy mice. In acute colitis, LL-TSLP delayed the disease activity index and lowered histological score and INF-γ production. In a DSS recovery model, LL-TSLP induced protective effect only if the strain was administered at the beginning of the colitis. At Day 4 of colitis we observed an induction of Treg by LL-TSLP. TSLP showed an anti-inflammatory protective role in colitis. The inventors have demonstrated that a short and early administration of LL-TSLP is more efficient than a long lasting treatment. Therefore oral administration of LL-TSLP could be a promising strategy to alleviate symptoms of IBD.

Materials & Methods

Mice Experiments

After acclimatization during at least 7 days, 6 weeks old C57BL/6 mice were fed daily during the whole experiment with PBS or with $10^9$~$5\times10^9$ Colony Forming Unity of LL-WT or LL-TSLP. At D0 colitis was induced by adding 2.5% (w/v) of Dextran Sulfate Sodium Salt (DSS) at a molecular weight of 36,000-50,000 (MPBio) to the drinking water for 4 days (DSS short) or 7 days (DSS acute and DSS recovery). The mice were sacrificed either at D4 (DSS short), D7 (DSS acute) or D12 (DSS recovery) after the DSS induction. For DSS recovery, DSS colitis induction was followed by 5 days of recovery with normal drinking water. As a control DSS mice have been fed during 12 days without DSS induction. Mice were monitored daily for weight loss, stool consistency, and fecal occult blood (Hemoccult, Beckman Coulter). Disease Activity Index (DAI) has been calculated according to the protocol established by Cooper et al in 1993 (Lab Investig, 69, 238-249). Mice have been sacrificed by cervical dislocation and Mesenteric Lymphatic Node (MLN) as well as the colon have been harvested.

Interleukin Production of Induced Lymphocyte

MLN isolated from mice were mashed and filtered (70 µm, BD biosciences). Lymphocytes in filtrate were count by flow cytometry (Accuri C6) and resuspended in culture medium (RPMI, Lonza) with 100 Unit of Streptomicin Penicilin, PAA Laboratories and 10% Fetal Calf Serum (FCS) (Lonza) at $25 \times 10^6$ cells/mL. Cell solutions were added to 24 well plates (Costar) pre-incubated 4 h with anti-CD3 and anti-CD28 antibodies, 4 µg/mL of each antibody (eBioscience) in PBS with 0.5% FCS. Plates were incubated 48 h at 37° C. 5% of CO2 and cytokine levels were assessed by ELISA (Mabtech).

Histological Assessment

For histological assessment, a colon sample located in the most inflamed area was fixed in 4% paraformaldehyde acid (sigma) and embedded in paraffin. Four micrometer sections were stained with hematoxylin/eosin and examined blindly according to the Ameho criteria.

Regulatory T Cells (Treg) Numeration $10^6$ cells have been taken from mashed MLN filtrates. Treg cells have been stained for CD4, CD32 and FoxP3 using a mouse regulatory T cell Staining Kit 1 (eBioscience). Cell samples have been run through flow cytometry (BD Accuri) and double positive cells for CD32 and FoxP3 among CD4 positive cells have been counted.

Statistic

All statistics and graphics have been performed on PrismGraphPad®. Results represent means±s.e.m. Statistical significance was determined by the Mann-Withney test for charts and by 2-way anova with Bonferroni post-test for curves * P<0.05,  P<0.01,  P<0.001.

Results

Figure 36:
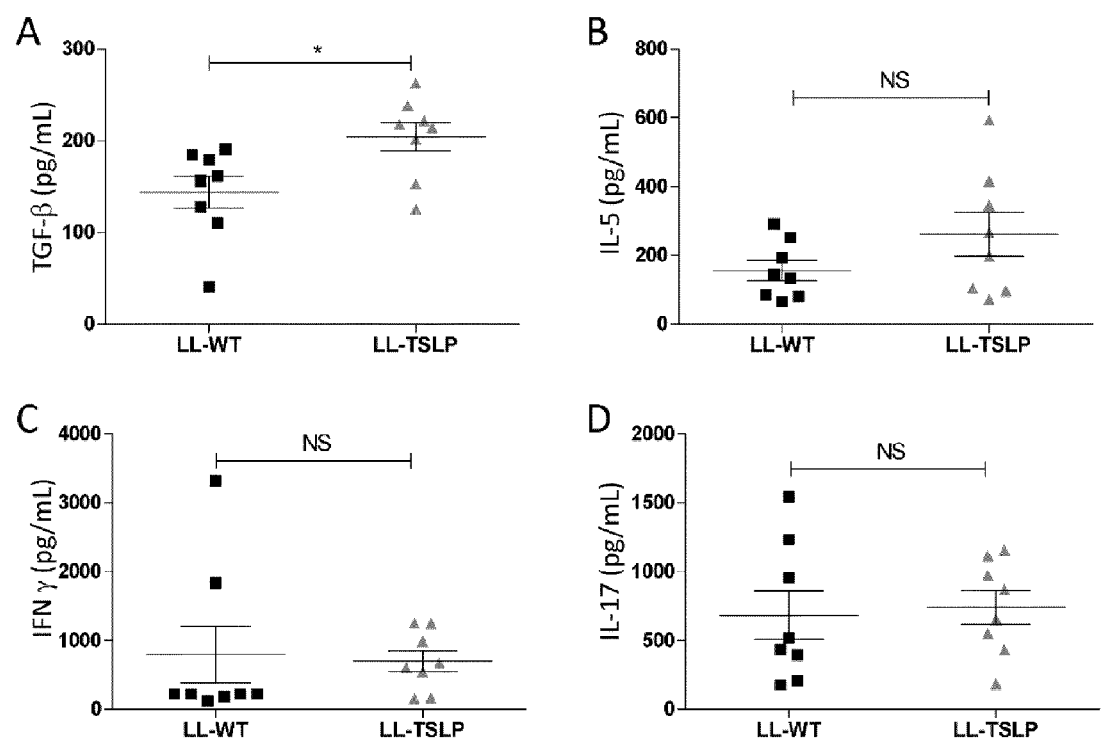
FIG. 36: Oral administration of LL-TSLP induced TGF β secretion. Mice were orally administered during five days consecutively with LL-TSLP or LL-wt during five days consecutively and then sacrificed. Concentrations of TGF-β (A), IL-25 (B), IFN-γ (C) and IL-17 (D) were measured in supernatants of anti-CD3 and anti-CD-28 activated cells from MLN.

Oral Administration of LL-TSLP Induced TGF-β Secretion by Activated Cells from Mesenteric Lymph Node of Healthy Mice To assess the basal effects of gut mucosal administration of TSLP on mice, two groups (n=8) of healthy animals received LL-WT, or LL-TSLP by oral route. Weight and DAI were daily monitored and scored. The inventors did not observe differences in these scores, showing no changes in the physiology of mice (data not shown). After 14 days of treatment, mesenteric lymph nodes (MLN) were removed and cells were activated with anti-CD3 and anti-CD-28 antibodies. The inventors detected a significantly (P<0.05) higher secretion of TGF-β when mice received LL-TSLP compare to mice orally dosed with LL-WT (FIG. 36-A). They did not observe any significant changes in IL-5, IFN-γ or IL-17 concentrations in cell supernatants (FIGS. 36-B, C and D). No differences have been seen on IL-10 either (data not shown). TSLP delivery through recombinant *L. lactis* in the intestinal lumen is able to trigger TGF-β secretion.

LL-TSLP Reduce Acute Inflammation

Figure 37:
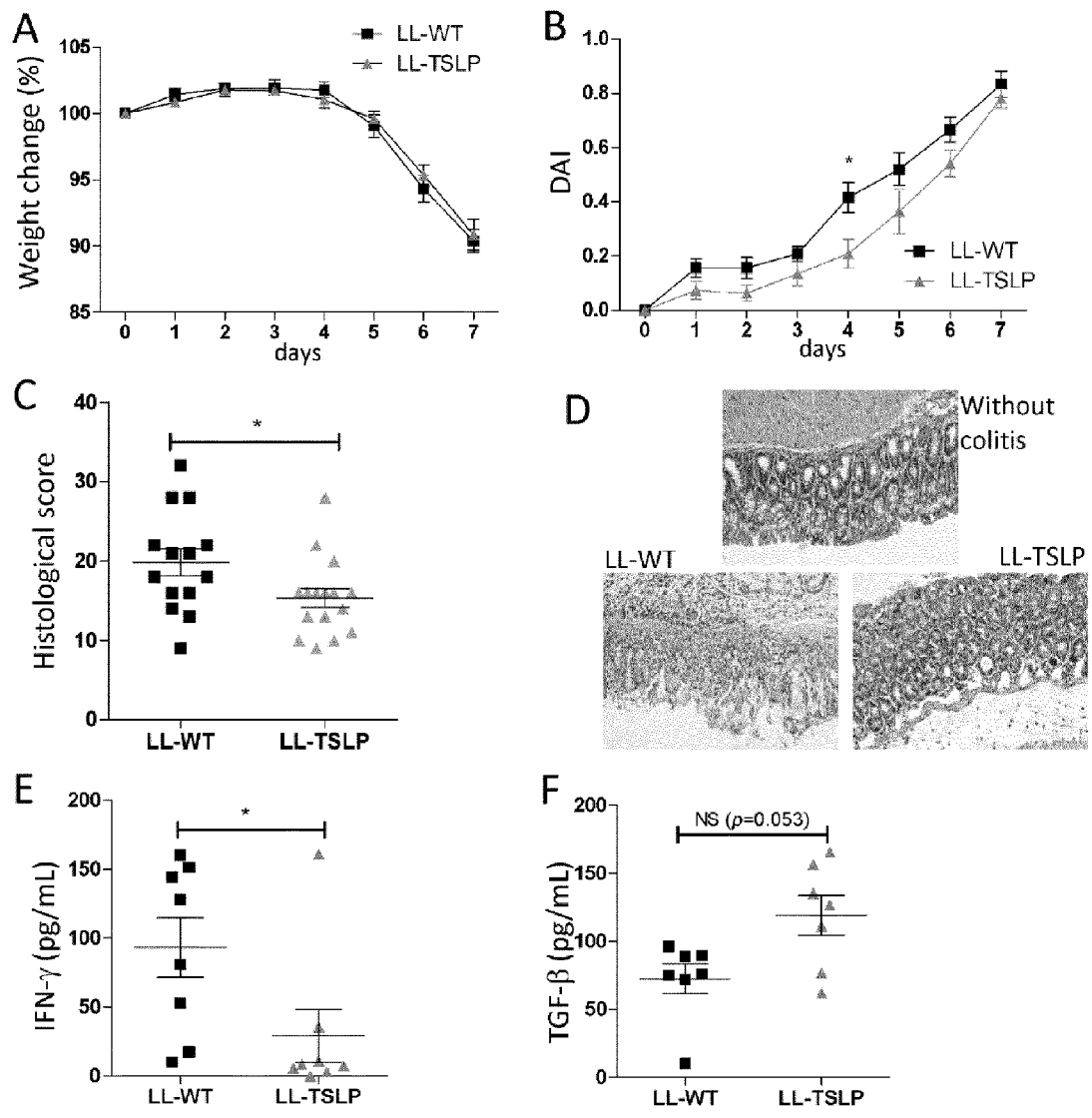
FIG. 37: Effects of oral administration of LL-TSLP on acute DSS-induced inflammation in mice. Mice were orally dosed with LL-WT or LL-TSLP five days prior DSS treatment until the end of study. Weight change (A) and Disease Activity Index (B) were monitored during the whole DSS treatment period. (C) Histological score of colon segment, (E) IFN-γ in colon washes and (F) TGF-β concentrations in supernatants of activated cells from MLN.

To determine the impact of local administration on intestinal inflammation, the inventors first performed an acute DSS-induced colitis model on mice that we orally administered with LL-TSLP or LL-WT seven days before and during colitis induction. They did not observe a difference in the weight loss of the two groups of mice (FIG. 37-A). Oral administration of LL-TSLP significantly decreased the DAI at D4, showing that TSLP-secreted *L. lactis* delayed clinical signs of colitis (FIG. 37-B), especially feces softening and bleeding. After seven days of inflammation, colon tissues were removed and several inflammation markers were analyzed. Histological score was reduced in presence of TSLP (FIGS. 37-C and D) demonstrating an intestinal epithelial protection by oral administration of LL-TSLP. The concentration of the pro-inflammatory cytokine IFN-γ in colon washes was also decreased after oral treatment with LL-TSLP (FIG. 37-E). The inventors did not detect any differences in the concentration of the pro-inflammatory IL-12 and the anti-inflammatory IL-10 in these colon washes (data not shown). They also observed an increase but not significant (p=0.053) of TGF-β in the supernatant of activated cells from MLNs. No differences were detected in IFN-γ, IL-5, IL-17 or IL-22 concentrations in the supernatant of activated cells from MLNs between the two conditions (data not shown).

Figure 38:
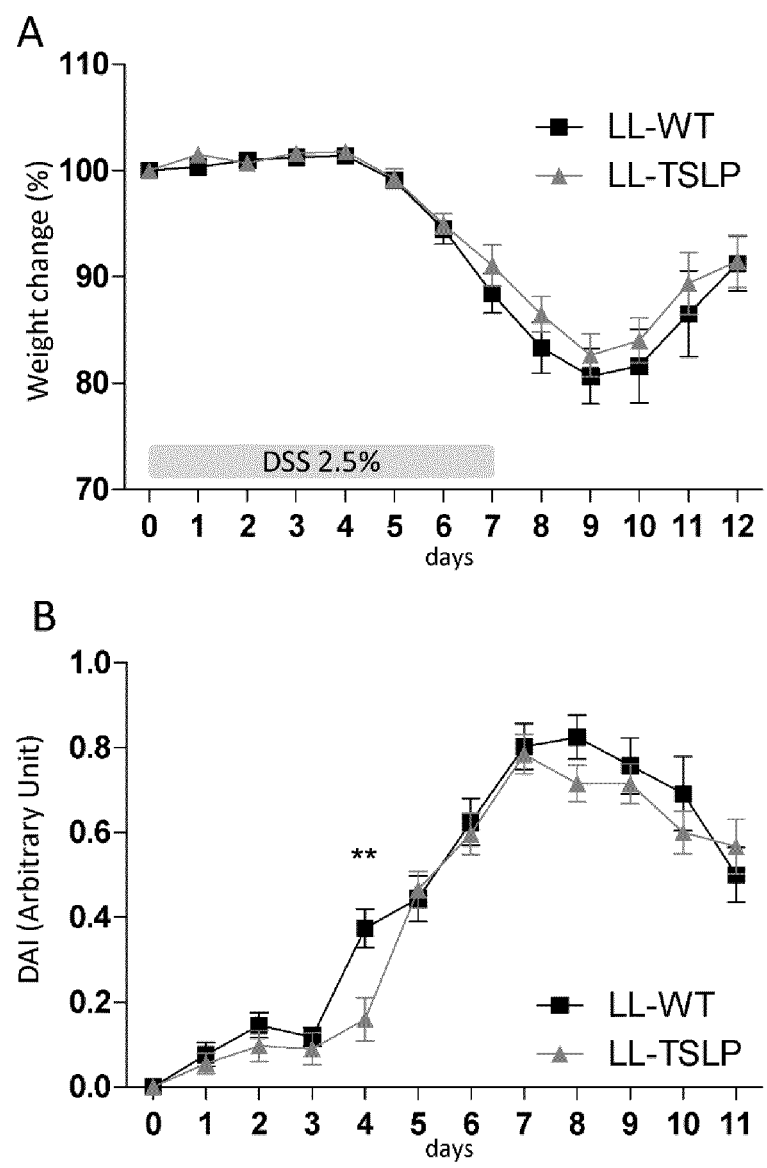
FIG. 38: Effects of oral administration of LL-TSLP on a DSS-recovery colitis model in mice. Mice were orally dosed with LL-WT or LL-TSLP five days prior DSS treatment until the end of study. After DSS treatment mice were allowed to recover for five days. Weight change (A) and DAI (B) were monitored during the DSS-induced colitis phase as well as during the following 5 days of recovery.

TSLP Decreased DAI in the Beginning of Inflammation but not in the Recovery Phase In order to test the involvement of TSLP in the healing process, the inventors performed an acute inflammation experiment followed by a recovery phase consisting of 5 days of water. Two groups of mice were treated seven days before colitis, along the inflammation as well as the recovery period with LL-WT or LL-TSLP. Oral TSLP administration did not modify the weight loss, which was around 20%, between the two group of mice (FIG. 38-A) but LL-TSLP significantly (P<0.01) decreased the DAI in the early phase of the inflammation (D4) as seen previously (FIG. 38-B), suggesting that TSLP had no effect in late inflammation and recovery phase.

Figure 39:
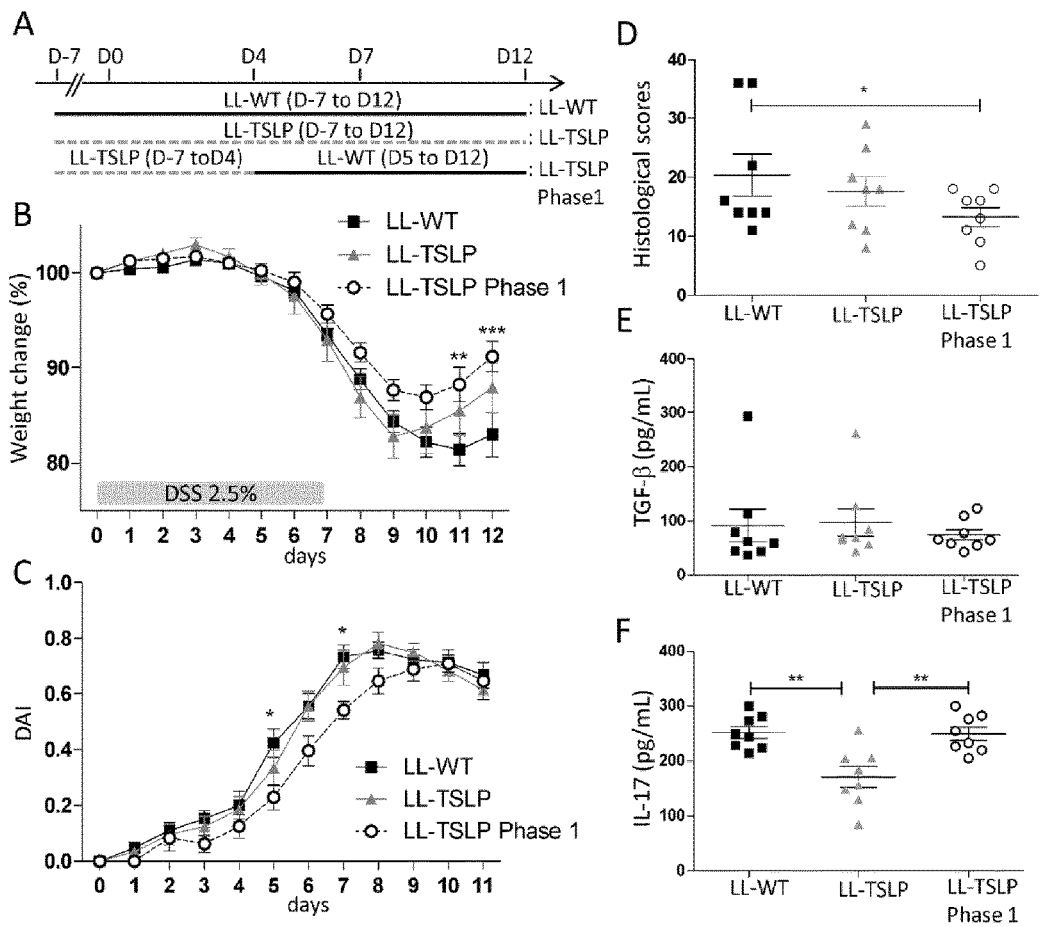
FIG. 39: Short and early LL-TSLP administration reduced inflammation during DSS-induced colitis. (A) Schematic representation of bacterial administration protocol. (B) Weight change. (C) DAI of mice treated with LL-WT, LL-TSLP or LL TSLP phase 1. (D) Histological score. (E) TGF-β and (F) IL-17 concentrations in supernatants of anti-CD3 and anti-CD-28 activated cells from MLN.

TSLP Delivery in the Early Phase of Inflammation Diminished the Loss Weight and the DAI To validate the effect of TSLP on the early phase of colitis, the inventors performed an acute inflammation followed by a recovery phase on groups of mice treated with LL-WT, LL-TSLP and a third group named LL-TSLP phase 1, corresponding to an oral administration of LL-TSLP from D-7 to D4 followed by oral administration of LL-WT from D5 to D12 (FIG. 39-A). As previously shown, the difference in weight loss between the LL-TSLP and LL-WT conditions was not significant. They observed a decrease of the weight loss when mice received early TSLP delivery, which was significantly (P<0.01 and P<0.001 respectively) different at D11 and D12 compare to the LL-WT condition (FIG. 39-B). Furthermore the inventors observed a reduced increase of DAI in the LL-TSLP phase 1 group, with significant (P<0.05) differences at D5 and D7 compare to the LL-WT DAI (FIG. 39-C). Histological scores were significantly reduced in the LL-TSLP Phase 1 group compared to the LL-WT group but not in the LL-TSLP group (FIG. 39-D). At D12, cells from MLN were activated but we did not detect any differences in TGF-β secretion in these cell supernatants between the three bacterial treatments (FIG. 39-E). However, the inventors did notice a significant (P<0.01) decrease of IL-17 secretion with LL-TSLP administration compare to LL-WT or LL-TSLP phase 1 (FIG. 39-F). These results demonstrated a decrease/amelioration of some colitis symptoms when TSLP was delivered at the early phase of the inflammation.

TSLP Induce a Treg Proliferation in the Early Phase of the Colitis

Figure 40:
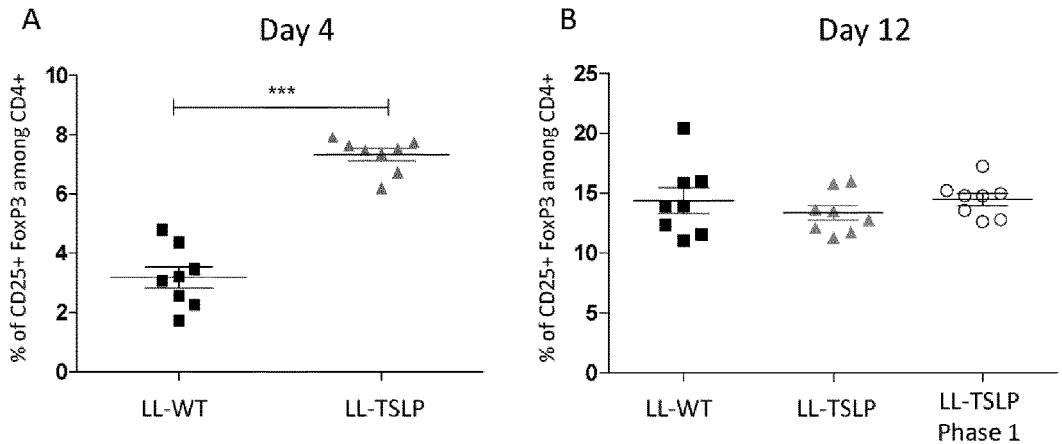
FIG. 40: Percentage of CD25+FoxP3+ among CD4+ population in MLN at day 4(A) and day 12(B).

In order to understand the effect of TSLP on the early phase of colitis the inventors analyzed the Treg proportion in MLN at day 4 and day 12 of colitis. The percentage of CD25+ FoxP3 Treg among the CD4+ population was significantly higher when mice were fed with LL-TSLP compared to control LL-WT at day 4 (FIG. 40-A). This difference in line with the differences in DAI scores observed between LL-TSLP treated mice and LL-WT at D4 (data not shown). No difference in percentage of CD25+ FoxP3 Treg among CD4+ population was observed at day 12 among the three groups (FIG. 40-B).

Discussion

In this study, effects of gut mucosal administration of TSLP in treatment for colitis have been investigated using the recombinant *L. lactis* strain LL-TSLP. In order to further understand the potential protective effect of TSLP on inflammation, the inventors have developed a strategy for TSLP delivery to the gut mucosal level by oral administration of Lactic Acid Bacteria (LAB) producing soluble functional TSLP. They constructed and characterized a *Lactococcus lactis* strain producing TSLP, LL-TSLP. After two weeks of LL-TSLP oral administration in healthy mice they observed an increase of TGF-β production by anti-CD3/anti-CD28 stimulated cells from mesenteric lymph nodes. In an acute DSS-induced inflammation model they showed that after 7 days of DSS, the DAI of mice treated with LL-TSLP tends to be lower during the 7 days of inflammation, despite absence of changes in weight loss. They observed a significant reduction of this score at D4, demonstrating the capacity of LL-TSLP to delay clinical signs at the beginning of colitis, especially feces softening and bleeding. Furthermore they showed that colonic tissue integrity measured by histological scores is less compromised within TSLP treated mice. Oral administration of LL-TSLP reduced the secretion of the pro-inflammatory cytokine, IFN-γ, showing that LAB-secreted TSLP protects the intestinal epithelium from damages induced by chemical treatment and modulates inflammation.

To assess the effect of LL-TSLP during the recovery phase, the inventors performed an acute colitis model followed by five days of remission. TSLP was delivered by LL-TSLP all along the experiment (inflammation+recovery phase). They did not show any differences in weight loss and histological scores after five days of water but we confirmed the decrease of DAI in the early phase at D4 of inflammation. The recovery phase is a complex process and addition of TSLP seems not to be sufficient to accelerate the decrease of markers of inflammation or intestinal epithelium repair.

Next, the inventors hypothesized that early treatment with LL-TSLP could be sufficient to decrease inflammation markers. A group of mice received LL-TSLP during seven days before and four days after the induction of colitis followed by LL-WT until the end of the experiment. TSLP delivery in the lumen at early phase, until D4, diminished the weight loss and significantly increased the weight gain at D11 and D12 compare to the LL-WT. Moreover it delayed and decreased the DAI (significantly at D5 and D7) and reduced the histological score. Therefore the inventors conclude that, short and early TSLP treatment allowed a better protection against colitis than a longer treatment as demonstrated by a lower severity as well as a delay in the disease.

To decipher by which mechanisms addition of TSLP leads to the colon protection in the early phase of the inflammation, the inventors sacrificed the mice at D4. At this time they observed a higher percentage of CD4+CD25+Foxp3+ cells in mice treated with LL-TSLP, suggesting a role of Treg cells in the delay of the outbreak of the disease. In human, TSLP-matured DC are able to induce the expansion and the differentiation of CD4+CD25+Foxp3+ cells.

The inventors hypothesized that addition of TSLP to the lumen allows an enhancement of gut homeostasis by a rise of the number of Treg cells which leads to a delay of the disease. Release of TSLP could act directly on Treg differentiation or indirectly. Indeed, TSLP is able to reinforce tight-junctions of lung epithelial cells by increasing several claudins and the occludin. In this manner, TSLP could protect gut epithelial integrity and increase the release of Retinoic acid and TGF-β by epithelial cells as well as the Treg expansion.

Finally, TSLP expression is reduced in colonic tissue of Crohn's disease patients and can be correlated to the failure of these patients to promote tolerogenic DCs in the gut. TSLP secretion by intestinal epithelial cells is dependant and regulated by commensal and probiotic bacteria. A novel treatment against Crohn disease is fecal transplantation. In the future, it could be very interesting to target fecal transplant that restore TSLP expression or complete actual treatment with probiotics that are able to increase TSLP secretion by epithelial cells to promote gut homeostasis and longer remission periods.

Example 3

Evaluation of the Immuno-Modulatory and Prophylactic Effects of Recombinant *L. Lactis* Strains Expressing IL-25 In Vivo In parallel, the inventors performed identical experiments (see material and methods of example 2) in order to test the effects of LL-IL-25 strain in the different mouse models of colitis established with LL-TSLP strain and another one: a DNBS model.

During acute DSS-induced colitis, LL-IL-25 was also able to delay clinical signs in inflamed mice treated at the beginning of the colitis. The inventors observed that LL-IL-25 strongly induced a Th2 response. As at the beginning of this project, they hypothesized that leading Th2 response could diminish Th1 or Th17-induced colitis in mice. However, they observed that *L. lactis* strain secreting a Th2-inducer cytokine (IL-25) was able to drive this response but not enough to protect mice from inflammation.

DSS models are frequently used to characterize innate immune response. For this reason, the inventors decided to test another inflammation model: a DNBS-induced colitis, known to drive a Th1 inflammation. They induced the inflammation by an intrarectal DNBS injection in mice. Once again the inflammation was too severe and several mice died. They have not observed mortality in group fed with IL-25-secreting strain, suggesting a protective role of LL IL-25 compared to the group fed with LL-WT. Moreover, LL-IL-25 force-feeding allows a lower weight loss at D1 and a smaller thickening of the colonic tissue was also observed, suggesting an important role of LL-IL-25 in the decrease of the inflammation.

In conclusion, these first preliminary results are very promising.

TABLE 1

Bacterial strains and plasmids used in this study

| Strains or plasmids | characteristics | Refs |
| --- | --- | --- |
| *L. lactis* MG1363 | Wild type, plasmid free | (Gasson 1983, J Bacteriol, 154, 1-9) |
| *L. lactis* NZ9000 | MG1363 (nisRK genes into chromosome), plasmid free | (Kuipers, P. G. et al. 1998, J Bactriol, 180, 3873-3881) |
| *L. casei* BL23 | Wild type, plasmid free | (Acedo-Felix and Perez-Martinez 2003, Int J Syst Evol Microniol, 53, 67-75) |
| *L. casei* nisRK | BL23 (nisRK genes into chromosome), plasmid free | (Hazebrouck, Pothelune et al. 2007, Microb Cell Fact, 6, 12) |
| *L. lactis* pNis-empty | *L. lactis* NZ9000 containing pNis-empty | (Bermudez-Humaran, Nouaille et al. 2007, Appl Environ Microbial, 73, 5300-5307) |
| *L. lactis* pNis-Nuc | *L. lactis* NZ9000 containing pNis-Nuc | (Bermudez-Humaran, Langella et al. 2003, Infect Immun, 71, 1887-1896) |
| *L. lactis* pNis-IL-25 | *L. lactis* NZ9000 containing pNis-IL-25 | this study |
| *L. lactis* pNis-IL-25-His | *L. lactis* NZ9000 containing pNis-IL-25-His | this study |
| *L. lactis* pNis-TSLP | *L. lactis* NZ9000 containing pNis-TSLP | this study |
| *L. lactis* pNis-TSLP-His | *L. lactis* NZ9000 containing pNis-TSLP-His | this study |
| *L. casei* pNis-Nuc | *L. casei* nisRK containing pNis-Nuc | laboratory collection |
| *L. casei* pNis-IL-25 | *L. casei* nisRK containing pNis-IL-25 | this study |
| *L. casei* pNis-IL-25-His | *L. casei* nisRK containing pNis-IL-25-His | this study |
| *L. casei* pNis-TSLP | *L. casei* nisRK containing pNis-TSLP | this study |
| *L. casei* pNis-TSLP-His | *L. casei* nisRK containing pNis-TSLP-His | this study |
| *L. lactis* pGroEL-Nuc | *L. lactis* MG1363 containing pGroEL-Nuc | laboratory collection |
| *L. lactis* pGroEL-IL-25 | *L. lactis* MG1363 containing pGroEL-IL-25 | this study |
| *L. lactis* pGroEL-IL-25-His | *L. lactis* MG1363 containing pGroEL-IL-25-His | this study |
| *L. lactis* pGroEL-TSLP | *L. lactis* MG1363 containing pGroEL-TSLP | this study |
| *L. lactis* pGroEL-TSLP-His | *L. lactis* MG1363 containing pGroEL-TSLP-His | this study |
| *L. casei* pDnaK-IL-25 | *L. casei* BL23 containing pDnaK-IL-25 | this study |
| *L. casei* pDnaK-IL-25-His | *L. casei* BL23 containing pDnaK-IL-25-His | this study |
| *L. casei* pDnaK-TSLP | *L. casei* BL23 containing pDnaK-TSLP | this study |
| *L. casei* pDnaK-TSLP-His | *L. casei* BL23 containing pDnaK-TSLP-His | this study |
| pMA-IL-25 | $Amp^R$, IL-25 synthetic gene | geneart |
| pMA-IL-25-His | $Amp^R$, IL-25-His synthetic gene | geneart |
| pMA-TSLP | $Amp^R$, TSLP synthetic gene | geneart |
| pMA-TSLP-His | $Amp^R$, TSLP-His synthetic gene | geneart |
| pMA-pDnaK-$SP_{P40}$ | $Amp^R$, promoter region of dnaK gene and signal peptide from P40 *L. casei* protein | geneart |
| pNis-empty | $Cm^R$; gene, expressed under $P_{nisA}$ encodes $SP_{USP45}$-no gene | |
| pNis-Nuc | $Cm^R$; gene, expressed under $P_{nisA}$ encodes $SP_{USP45}$-NucB | |
| pNis-IL-25 | $Cm^R$; gene, expressed under $P_{nisA}$ encodes $SP_{USP45}$-IL-25 | |
| pNis-IL-25-HIS | $Cm^R$; gene, expressed under $P_{nisA}$ encodes $SP_{USP45}$-IL-25-His | |
| pNis-TSLP | $Cm^R$; gene, expressed under $P_{nisA}$ encodes $SP_{USP45}$-TSLP | |
| pNis-TSLP-HIS | $Cm^R$; gene, expressed under $P_{nisA}$ encodes $SP_{USP45}$-TSLP-His | |
| pGroEL-Nuc | $Cm^R$; gene, expressed under $P_{groEL}$ encodes $SP_{EXP4}$-NUC | |
| pGroEL-IL-25 | $Cm^R$; gene, expressed under $P_{groEL}$ encodes $SP_{EXP4}$-IL-25 | |
| pGroEL-IL-25-HIS | $Cm^R$; gene, expressed under $P_{groEL}$ encodes $SP_{EXP4}$-IL-25-His | |
| pGroEL-TSLP | $Cm^R$; gene, expressed under $P_{groEL}$ encodes $SP_{EXP4}$-TSLP | |
| pGroEL-TSLP-HIS | $Cm^R$; gene, expressed under $P_{groEL}$ encodes $SP_{EXP4}$-TSLP-His | |
| pDnaK-IL-25 | $Cm^R$; gene, expressed under $P_{dnaK}$ encodes $SP_{P40}$-IL-25 | |
| pDnaK-IL-25-His | $Cm^R$; gene, expressed under $P_{dnaK}$ encodes $SP_{P40}$-IL-25-His | |

TABLE 1-continued

Bacterial strains and plasmids used in this study

| Strains or plasmids | characteristics | Refs |
|---|---|---|
| pDnaK-TSLP | Cm$^R$; gene, expressed under P$_{dnaK}$ encodes SP$_{P40}$-TSLP | |
| pDnaK-TSLP-His | Cm$^R$; gene, expressed under P$_{dnaK}$ encodes SP$_{P40}$-TSLP-His | |

The invention claimed is:

1. A recombinant *Lactococcus lactis* bacterium, wherein the bacterium comprises an expression cassette comprising a heterologous nucleotide sequence encoding a cytokine selected from the group consisting of thymic stromal lymphopoietin (TSLP) and interleukin-25 (IL-25), wherein the heterologous nucleotide sequence encoding the cytokine is under the control of a promoter of the GroESL operon of *Lactococcus lactis*.

2. The recombinant *Lactococcus lactis* bacterium according to claim 1, wherein the expression cassette further comprises a nucleotide sequence encoding an extracellular addressing peptide.

3. The recombinant *Lactococcus lactis* bacterium according to claim 1, wherein the TSLP is human TSLP.

4. The recombinant *Lactococcus lactis* bacterium according to claim 1, wherein the IL-25 is human IL-25.

5. A pharmaceutical or probiotic composition comprising a recombinant *Lactococcus lactis* bacterium according to claim 1.

6. The pharmaceutical or probiotic composition according to claim 5, wherein the composition comprises a recombinant *Lactococcus lactis* bacterium secreting TLSP and/or a recombinant *Lactococcus lactis* bacterium secreting IL-25.

7. The pharmaceutical or probiotic composition according to claim 5, the composition further comprising an anti-inflammatory or immune-modulatory drug.

8. A food composition comprising a recombinant *Lactococcus lactis* bacterium according to claim 1.

* * * * *

UNITED STATES PATENT AND TRADEMARK OFFICE
CERTIFICATE OF CORRECTION

PATENT NO. : 10,238,697 B2
APPLICATION NO. : 15/565958
DATED : March 26, 2019
INVENTOR(S) : Philippe Langella et al.

Page 1 of 1

It is certified that error appears in the above-identified patent and that said Letters Patent is hereby corrected as shown below:

In the Specification

<u>Column 12,</u>
Line 33, "pF." should read --μF.--.

Signed and Sealed this
Seventeenth Day of September, 2019

Andrei Iancu
*Director of the United States Patent and Trademark Office*

SEQUENCE LISTING

<160> NUMBER OF SEQ ID NOS: 8

<210> SEQ ID NO 1
<211> LENGTH: 82
<212> TYPE: DNA
<213> ORGANISM: Lactococcus lactis

<400> SEQUENCE: 1

```
cttgactaaa tctgaccatt gagataaaat aagaatatgt tagcactcaa ctattaagag      60
tgctaaaaat aaaaaatgga gg                                              82
```

<210> SEQ ID NO 2
<211> LENGTH: 82
<212> TYPE: DNA
<213> ORGANISM: Lactococcus lactis

<400> SEQUENCE: 2

```
cttgactaaa tctgaccatt gagataaaat aagaatatgt tagcacacaa ctattaagag      60
tgctaaaaat aaaaaatgga gt                                              82
```

<210> SEQ ID NO 3
<211> LENGTH: 83
<212> TYPE: DNA
<213> ORGANISM: Lactococcus lactis

<400> SEQUENCE: 3

```
cttgactaaa tctgaccatt gagataaaat aagaatatgt tagcactcgt ttaataagag      60
tgctaaaaaa taaaaaatgg agg                                             83
```

<210> SEQ ID NO 4
<211> LENGTH: 83
<212> TYPE: DNA
<213> ORGANISM: Lactococcus lactis

<400> SEQUENCE: 4

```
cttgactaaa tctgaccatt gagataaaat aagaatatgt tagcactcgt ttaacaagag      60
tgctaaaaaa taaaaaatgg agg                                             83
```

<210> SEQ ID NO 5
<211> LENGTH: 159
<212> TYPE: PRT
<213> ORGANISM: Homo sapiens

<400> SEQUENCE: 5

```
Met Phe Pro Phe Ala Leu Leu Tyr Val Leu Ser Val Ser Phe Arg Lys
1               5                   10                  15

Ile Phe Ile Leu Gln Leu Val Gly Leu Val Leu Thr Tyr Asp Phe Thr
            20                  25                  30

Asn Cys Asp Phe Glu Lys Ile Lys Ala Ala Tyr Leu Ser Thr Ile Ser
```

```
              35                  40                  45
Lys Asp Leu Ile Thr Tyr Met Ser Gly Thr Lys Ser Thr Glu Phe Asn
 50                  55                  60

Asn Thr Val Ser Cys Ser Asn Arg Pro His Cys Leu Thr Glu Ile Gln
 65                  70                  75                  80

Ser Leu Thr Phe Asn Pro Thr Ala Gly Cys Ala Ser Leu Ala Lys Glu
                 85                  90                  95

Met Phe Ala Met Lys Thr Lys Ala Ala Leu Ala Ile Trp Cys Pro Gly
                100                 105                 110

Tyr Ser Glu Thr Gln Ile Asn Ala Thr Gln Ala Met Lys Lys Arg Arg
                115                 120                 125

Lys Arg Lys Val Thr Thr Asn Lys Cys Leu Glu Gln Val Ser Gln Leu
130                 135                 140

Gln Gly Leu Trp Arg Arg Phe Asn Arg Pro Leu Leu Lys Gln Gln
145                 150                 155

<210> SEQ ID NO 6
<211> LENGTH: 177
<212> TYPE: PRT
<213> ORGANISM: Homo sapiens

<400> SEQUENCE: 6

Met Arg Glu Arg Pro Arg Leu Gly Glu Asp Ser Ser Leu Ile Ser Leu
  1               5                  10                  15

Phe Leu Gln Val Val Ala Phe Leu Ala Met Val Met Gly Thr His Thr
                 20                  25                  30

Tyr Ser His Trp Pro Ser Cys Cys Pro Ser Lys Gly Gln Asp Thr Ser
                 35                  40                  45

Glu Glu Leu Leu Arg Trp Ser Thr Val Pro Val Pro Pro Leu Glu Pro
 50                  55                  60

Ala Arg Pro Asn Arg His Pro Glu Ser Cys Arg Ala Ser Glu Asp Gly
 65                  70                  75                  80

Pro Leu Asn Ser Arg Ala Ile Ser Pro Trp Arg Tyr Glu Leu Asp Arg
                 85                  90                  95

Asp Leu Asn Arg Leu Pro Gln Asp Leu Tyr His Ala Arg Cys Leu Cys
                100                 105                 110

Pro His Cys Val Ser Leu Gln Thr Gly Ser His Met Asp Pro Arg Gly
                115                 120                 125

Asn Ser Glu Leu Leu Tyr His Asn Gln Thr Val Phe Tyr Arg Arg Pro
130                 135                 140

Cys His Gly Glu Lys Gly Thr His Lys Gly Tyr Cys Leu Glu Arg Arg
145                 150                 155                 160

Leu Tyr Arg Val Ser Leu Ala Cys Val Cys Val Arg Pro Arg Val Met
                165                 170                 175

Gly

<210> SEQ ID NO 7
<211> LENGTH: 161
<212> TYPE: PRT
<213> ORGANISM: Homo sapiens

<400> SEQUENCE: 7

Met Tyr Gln Val Val Ala Phe Leu Ala Met Val Met Gly Thr His Thr
  1               5                  10                  15

Tyr Ser His Trp Pro Ser Cys Cys Pro Ser Lys Gly Gln Asp Thr Ser
                 20                  25                  30
```

```
Glu Glu Leu Leu Arg Trp Ser Thr Val Pro Val Pro Leu Glu Pro
        35                  40              45

Ala Arg Pro Asn Arg His Pro Glu Ser Cys Arg Ala Ser Glu Asp Gly
        50                  55              60

Pro Leu Asn Ser Arg Ala Ile Ser Pro Trp Arg Tyr Glu Leu Asp Arg
65              70                  75                      80

Asp Leu Asn Arg Leu Pro Gln Asp Leu Tyr His Ala Arg Cys Leu Cys
                85                  90                  95

Pro His Cys Val Ser Leu Gln Thr Gly Ser His Met Asp Pro Arg Gly
            100                 105             110

Asn Ser Glu Leu Leu Tyr His Asn Gln Thr Val Phe Tyr Arg Arg Pro
        115                 120                 125

Cys His Gly Glu Lys Gly Thr His Lys Gly Tyr Cys Leu Glu Arg Arg
        130             135                 140

Leu Tyr Arg Val Ser Leu Ala Cys Val Cys Val Arg Pro Arg Val Met
145             150                 155                 160

Gly

<210> SEQ ID NO 8
<211> LENGTH: 25
<212> TYPE: PRT
<213> ORGANISM: Lactococcus lactis

<400> SEQUENCE: 8

Met Lys Lys Ile Asn Leu Ala Leu Leu Thr Leu Ala Thr Leu Met Gly
1               5                   10                  15

Val Ser Ser Thr Ala Val Val Phe Ala
            20                  25
```